United States Patent
Dessain et al.

(10) Patent No.: US 7,491,530 B2
(45) Date of Patent: Feb. 17, 2009

(54) FUSION PARTNER CELLS AND USES THEREOF

(75) Inventors: Scott K. Dessain, Wynnewood, PA (US); Robert A. Weinberg, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 360 days.

(21) Appl. No.: 10/324,114

(22) Filed: Dec. 18, 2002

(65) Prior Publication Data

US 2003/0224490 A1 Dec. 4, 2003

Related U.S. Application Data

(60) Provisional application No. 60/375,236, filed on Apr. 24, 2002, provisional application No. 60/355,236, filed on Feb. 7, 2002, provisional application No. 60/349,872, filed on Jan. 17, 2002, provisional application No. 60/341,567, filed on Dec. 18, 2001.

(51) Int. Cl.
| | |
|---|---|
| C12N 5/06 | (2006.01) |
| C12N 5/08 | (2006.01) |
| C12N 5/10 | (2006.01) |
| C12N 5/02 | (2006.01) |
| C12N 5/12 | (2006.01) |
| C12N 5/18 | (2006.01) |
| C12N 5/22 | (2006.01) |
| C12N 5/24 | (2006.01) |
| C12N 5/26 | (2006.01) |
| C12N 5/28 | (2006.01) |

(52) U.S. Cl. ............... 435/325; 435/355; 435/372.1; 435/372.2; 435/374; 435/375

(58) Field of Classification Search ............ None
See application file for complete search history.

(56) References Cited

U.S. PATENT DOCUMENTS

| | | | |
|---|---|---|---|
| 5,686,306 A | 11/1997 | West et al. | |
| 5,916,771 A | 6/1999 | Hori et al. | |
| 5,939,598 A | 8/1999 | Kucherlapati et al. | |
| 5,985,615 A | 11/1999 | Jakobovits et al. | |
| 5,998,209 A | 12/1999 | Jokobovits et al. | |
| 6,075,181 A | 6/2000 | Kucherlapati et al. | |
| 6,091,001 A | 7/2000 | Jakobovits et al. | |
| 6,114,598 A | 9/2000 | Kucherlapati et al. | |
| 6,130,364 A | 10/2000 | Jakobovits et al. | |
| 6,150,584 A | 11/2000 | Kucherlapati et al. | |
| 6,162,963 A | 12/2000 | Kucherlapati et al. | |
| 6,207,418 B1 | 3/2001 | Hori et al. | |
| 6,235,883 B1 | 5/2001 | Jakobovits et al. | |
| 2002/0045219 A1* | 4/2002 | Dessain et al. | 435/70.21 |

FOREIGN PATENT DOCUMENTS

| WO | WO 02/04607 A1 | 1/2002 |
|---|---|---|
| WO | WO 02/010352 | 2/2002 |
| WO | WO 02/10352 A2 | 2/2002 |
| WO | WO 03/052082 | 6/2003 |

OTHER PUBLICATIONS

Chen et al. Unveiling the mechanisms of cell-cell fusion. Science 308: 369-373, 2005.*
Nelson et al. Monoclonal antibodies. J. Clin. Path: Mol. Pathol. 53:111-117, 2000.*
Ehlers et al. Combining two mutations of human interleukin-6 that affect gp130 activation results in a potent interleukin-6 receptor antagonist on human myeloma cells. Journal of Biological Chemistry 270(14): 8185-8163, 1995.*
Devroe et al. Retrovirus-delivered siRNA. BMC Biotechnology 2:15, available from http://www.biomedcentral.com/1472-6750/2/15. Aug. 2002.*
Harris et al. Increased frequency of both total and specific monoclonal antibody producing hybridomas using a fusion partner that constitutively expresses recombinant IL-6. J. Immunological Methods 148: 199-207, 1992.*
Sontag et al. The interaction of SC40 small tumor antigen with protein phosphatase 2A stimulates the Map Kinase pathway and induces cell proliferation. Cell 75: 887-897, 1993.*
Yin et al. Involvement of IL-6 signal transducer gp130 in IL-11 mediated signal transduction. J. Immunology 151(5):2555-2561, 1993.*
Abstract of Nho et al (Blood, 2000, vol. 96, p. 752a).*
Carroll, W.L. et al., Mouse × human heterohybridomas as fusion partners with human B cell tumors. J Immunol Methods. May 1, 1986;89(1):61-72.
Dessain, S.K. et al., High efficiency creation of human monoclonal antibody-producing hybridomas. J Immunol Methods. Aug. 2004;291(1-2):109-22.
Larrick, J.W. et al., Characterization of human hybridomas secreting antibody to tetanus toxoid. Proc Natl Acad Sci U S A. Oct. 1983;80(20):6376-80.
Ajiro, K. et al., Species-Specific Suppression of Histone H1 and H2B Production in Human/Mouse Hybrids, *Proc. Natl. Acad. Sci. USA* 75:5599-5603, 1978.
Borth, N. et al., Analysis of Changes During Subclone Development and Ageing of Human Antibody-Producing Heterohybridoma Cells By Northern Blot and Flow Cytometry, *J. Biotechnol.* 67:57-66, 1999.

(Continued)

*Primary Examiner*—Karen A Canella
(74) *Attorney, Agent, or Firm*—Wolf, Greenfield & Sacks, P.C.

(57) ABSTRACT

The present invention provides in one aspect novel fusion partner cells that ectopically express one or more genes that alter the phenotype of a hybrid cell made from a fusion of the fusion partner cell and a fusion cell, hybrid cell lines produced using the fusion partner cells. The invention in another aspect provides antibodies produced by certain hybrid cell lines, and compositions containing one or a combination of such antibodies or antigen-binding fragments thereof. The invention also provides in another aspect methods of using the antibodies or antigen-binding fragments thereof for diagnosis and treatment of diseases characterized by the antigens specifically bound by the antibodies.

24 Claims, 10 Drawing Sheets

OTHER PUBLICATIONS

Cieplinski, W. et al., Non-Random Human Chromosome Distribution in Human-Mouse Myeloma Somatic Cell Hybrids, *Cytogenet. Cell Genet.* 35:93-99, 1983.

Croce, C.M. et al., Unidirectional Loss of Human Chromosomes in Rat-Human Hybrids, *Exp. Cell Res.* 79:461-463, 1973.

Glasky, M.S. et al., Stability of Specific Immunoglobulin Secretion by EBV-Transformed Lymphoblastoid Cells and Human-Murine Heterohybridomas, *Hybridoma* 8:377-389, 1989.

Goss, S.J. et al., New Method for Mapping Genes in Human Chromosomes, *Nature* 255:680-684, 1975.

Groves, D.J. et al., Veterinary Sources of Nonrodent Monoclonal Antibodies: Interspecific and Intraspecific Hybridomas, *Hybridoma* 19:201-214, 2000.

Handmaker, SD, Chromosome Behaviour in Human-Mouse Somatic-Cell Hybrids, *Biochem. J.* 124:37P, 1971.

Harris, J.F. et al., Spontaneous and Radiation-Induced genetic Instability of Heteromyeloma Hybridoma Cells, *Mol. Biol. Med.* 7:485-493, 1990.

Huebner, K. et al., Suppression of Replication of SV40 and Polyoma Virus in Mouse-Human Hybrids, *Cell* 11:25-33, 1977.

Jessup, C.F. et al., Preparation of Human-Mouse Heterohybridomas Against an Immunising Antigen, *J. Immunol. Methods* 246:187-202, 2000.

Kawano, M. et al., Autocrine Generation and Requirement of BSF-2/IL-6 For Human Multiple Myelomas, *Nature* 332:83-85, 1988.

Miggiano, V. et al., Hybrids Between Human Leukocytes and a Mouse Cell Line: Production and Characterization, *Wistar Inst Symp Monogr* 9:61-76, 1969.

Nabholz, M et al., Genetic Analysis With Human-Mouse Somatic Cell Hybrids, *Nature* 223:358-363, 1969.

Norum, R.A. et al., Non-Random Loss of Human Markers from Man-Mouse Somatic Cell Hybrids, *Nature* 251:72-74, 1974.

Raison, R.L. et al., Loss of Secretion in Mouse-Human Hybrids Need Not Be Due to the Loss of a Structural Gene, *J. Exp. Med.* 156:1380-1389, 1982.

Rushton, A.R., Quantitative Analysis of Human Chromosome Segregation in Man-Mouse Somatic Cell Hybrids, *Cytogenet. Cell Genet.* 17:243-253, 1976.

Van Snick, J., Interleukin-6: An Overview, *Annu. Rev. Immunol.* 8:253-278, 1990.

Guo, Y. et al., Effective Tumor Vaccine Generated by Fusion of Hepatoma Cells with Activated B Cells. *Science*, 263:518-520, 1994.

Berube, N. et al., The Genetics of Cellular Scenescence, *Am. J. Hum. Genet.* 62:000 (1998).

Borrebaeck, C. et al, Does Endogenous Glycosylation Prevent the Use of Mouse Monoclonal Antibodies as Cancer Therapeutics?, *Immun. Today* 14(10):477 (1993).

Borth, N. et al., Analysis of changes during subclone development and ageing of human antibody-producing heterohybridoma cells by Northern blot and flow cytometry, *J. Biotech.* 67:57 (1999).

Burk, K. et al., Establishment of a Human Plasma Cell Line in Vitro, *Cancer Research* 38:2503 (1978).

Chiorazzi, N. et al., Use of Epstein-Barr Virus-Transformed B Cell Lines for the Generation of Immunoglobulin-Producing Human B Cell Hybridomas, *J. Exp. Med.* 156:930 (1982).

Cote, R., et al., Generation of Human Monoclonal Antibodies Reactive with Cellular Antigens, *Proc. Natl. Acad. Sci. USA* 80(7):2026 (1983) (Abstract Only).

Croce, et al., Production of Human Hybridomas Secreting Antibodies to Measles Virus, *Nature* 288:4 (1980).

Drexler, H. et al., False Human Hematopoietic Cell Lines: Cross Contaminations and Misinterpretations, *Leukemia* 13(10):1601 (1999) (Abstract Only).

Ebeling, S. et al., Human Chromosome 21 Determines Growth Factor Dependence in Human/Mouse B-Cell Hybridomas, *Cancer Res.* 58:2863 (1998).

Edwards, P. et al., A Human-Human Hybridoma System Based on a Fast-Growing Mutant of the ARH-77 Plasma Cell Leukemia-Derived Line, *Eur. J. Immunol.* 12:641 (1982).

Gooding, R. et al., Phenotypic and Molecular Analysis of Six Human Cell Lines Derived From Patients with Plasma Cell Dyscrasia, *Br. J. Haemotology* 106:669 (1999).

Harris, H. et al., Mitosis in Hybrid Cells Derived From Mouse and Man, *Nature* 207:606 (1965).

Harris, J. et al., Increased Frequency of Both Total and Specific Monoclonal Antibody Producing Hybridomas Using a Fusion Partner That Constitutively Expresses Recombinant IL-6, *J. Immunol. Methods* 148:199 (1992).

Harris, N. et al., Plasma Cell Surface Antigen on Human Blood Lymphocytes, *Nature* 250:507 (1974).

Hirano, T. et al. Complementary DNA for a Novel Human Interleukin (BSF-2) that Induces B Lymphocytes to Produce Immunoglobulin, *Nature* 324:73 (1986).

Jessup, C. et al., Preparation of Human-Mouse Heterohybridomas Against an Immunising Antigen, *J. Immunol. Methods* 246:187 (2000).

Karpas, A. et al., A Human Myeloma Cell Line Suitable for the Generation of Human Monoclonal Antibodies, *PNAS* 98(4):1799 (2001).

Kayhty, H. et al., Pneumococcal Polysaccharide-Meningococcal Outer Membrane Protein Complex Conjugate Vaccine is Immunogenic in Infants and Chrildren, *J. Infectious Disease* 172:1273 (1995).

Koropatnick, J. et al., Extensive Loss of Human DNA Accompanies Loss of Antibody Production in Heteromyeloma Hybridoma Cells, *Mol. Biol. Med.* 5:69 (1988).

Kozbor, D. et al., Fusion Partners for Production of Human Monoclonal Antibodies, *Wistar Institute of Anatomy and Biology* p. 21.

Kozbor, D. et al., A Comparative Analysis of the Phenotypic Characteristics of Available Fusion Partners for the Construction of Human Hybridomas, *Hybridoma* 2(1):7 (1983).

Liu et al., Constitutive and Regulated Expression of Telomerase Reverse Transcriptase (hTERT) in Human Lymphocytes, *Proc. Natl. Acad. Sci. USA* 96:5147 (1999).

Labella, T., et al., Asynchronous DNA Replication and Asymmetrical Chromosome Loss in Chinese Hamster-Mouse Somatic Cell Hybrids, *Somatic Cell Genet.* 2(1):1 (1976) (Abstract Only).

Liu, Q. et al., Adenovirus-Mediated Delivery of p53 Results in Substanital Apoptosis to Myeloma Cells and is not Cytotoxic to Flow-Sorted CD34+ Hematopoietic Progenitor Cells and Normal Lymphocytes, *Experimental Hematology* 28:1354 (2000).

Massicotte, H. et al., Influence of Fusion Cell Ration and Cell Plating Density on Production of Human-Human Hybriomas Secreting Anti-DNA Autoantibodies from Patients with Systemic Lupus Erythematosus, *Hybridoma* 3(3):215 (1984).

Matsuoka, Y. et al., Production of Free Light Chains of Immunoglobulin by a Hematopoietic Cell Line Derived from a Patient with Multiple Myelomas, *PSEBM* 125:1246 (1967).

Merten, O. et al., Stabilizing Effect on Reduced Cultivation Temperature on Human X Mouse Hybridomas, *Develop. Biol. Standard* 60:509 (1985).

Miller, O., et al., Expression of Human and Suppression of Mouse Nucleolus Organizer Activity in Mouse-Human Somatic Cell Hybrids, *Proc. Natl. Acad. Sci. USA* 73(12):4531 (1976) (Abstract Only).

Miller, O. et al., Mitotic Separation of Two Human X-Linked Genes in Man-Mouse Somatic Cell Hybrids, *Proceedings of the Natl. Acad. Sci.* 68(1):116 (1971).

Nilsson, K. et al., Established Immunoglobulin Producing Myeloma (IgE) and Lymphoblastoid (IgG) Cell Lines from an IgE Myeloma Patient, *Clin. Exp. Immunol.* 7:477 (1970).

Nowinski, R. et al., Human Monoclonal Antibody Against Forssman Antigen, *Science* 210:537 (1980).

Olsson, L. et al., Antibody Producing Human-Human Hybridomas, *J. Immunol. Methods* 61:17 (1983).

Human-Human Hybridomas Producing Monoclonal Antibodies of Predefined Antigenic Specificity, *Proc. Natl. Acad. Sci. USA* 77(9):5429 (1980).

Ostberg, L. et al., Human X (Mouse X Human) Hybridomas Stably Producing Human Antibodies, *Hybridoma* 2(4):361 (1983).

Pellat-Deceunynk, C. et al., Human Myeloma Cell Lines as a Tool for Studying the Biology of Multiple Myeloma: A Reappraisal 18 Years After, *Blood* 86(10):4001 (1995).

Pickering, J., et al., A Human Myeloma Cell Line that does not Express Immunoglobulin but Yields a High Frequency of Antibody-Secreting Hybridomas, *Dept. of Microbiol. and Immunol. and Surgery* p. 406 (1982).

Posner, M. et al., The Construction and Use of a Human-Mouse Myeloma Analogue Suitable for the Routine Production of Hybridomas Secreting Human Monoclonal Antibodies, *Hybridoma* 6(6):611 (1987).

*R & D Systems 1999 Catalog*, Interleukin 6 (1999).

Ritts, R. et al., Establishment and Characterization of a Human Non-Secretory Plasmacytoid Cell Line and its Hybridization with Human B Cells, *Int. J. Cancer* 31:133 (1983).

Rowley, M. et al., Heterogeneity in therapeutic Response of Genetically Altered Myeloma Cell Lines to Interleukin 6, Dexamethasone, Doxorubicin, and Melphalan, *Blood* 96(9):3175 (2000).

Rushton, A., Quantitative Analysis of Human Chromosome Segregation in Man-Mouse Somatic Cell Hybrids, *Cytogenet. Cell Genet.* 17:243 (1976).

Schall, D., et al., Kinetics of Human Chromosome Loss from 3T3-Human Hybrid Cells, *Somatic Cell Genet.* 4(6):661 (1978) (Abstract Only).

Schlom, J., et al., Generation of Human Monoclonal Antibodies Reactive with Human Mammary Carcinoma Cells, *Proc. Natl. Acad. Sci. USA* 77(11):6841 (1980).

Schwaber, J., Human Lymphocyte—Mouse Myeloma Somatic Cell Hybrids: Selective Hybrid Formation, *Somatic Cell Genetics*, 3:295 (1977).

Shay, J., Human Hybridomas and Monoclonal Antibodies, *Dept. of Cell Biol.*, Univ. of TX p. 5.

Shirahata, S., et al., Cell Hybridization, Hydridomas, and Human Hybridomas, *Methods Cell Biol.* 57:111 (1998) (Abstract Only).

Shulman, M. et al., A Better Cell Line for Making Hybridomas Secreting Specific Antibodies, *Nature* 276:269 (1978).

Shoenfeld, Y et al., Polyspecificity of Monoclonal Lupus Autoantibodies Produced by Human-Human Hybridomas, *N.E. J. Med.* 308(8):414 (1983).

Thompson, K. et al., The Efficient Production of Stable, Human Monoclonal Antibody-Secreting Hybridomas from EBV-Transformed Lymphocytes Using the Mouse Myeloma X63-Ag8.653 as a Fusion Partner, *J. Immunol. Methods* 94:7 (1986).

Urashima, M. et al., Interlekin-6 Overcomes p21 WAF1 Upregulation and G1 Growth Arrest Induced by Dexamethasone and Interferon-y in Multiple Myeloma Cells, *Blood* 90(1):279 (1997).

Urashima, M., et al., Interleukin-6 Promotes Multiple Myeloma Cell Growth via Phosphorylation of Retinoblastoma Protein, *Blood* 88(6):2219 (1996).

Yasukawa, K., et al., Structure and Expression of Human B Cell Stimulatory Factor-2 (BSF-2/IL-6) Gene, *EMBO J.* 6(10):2939 (1987).

Handmaker, S.D. Chromosome behaviour in human-mouse somatic-cell hybrids. Biochem J. Oct. 1971;124(5):37P.

Kalantarov, G.F. et al., Development of a fusion partner cell line for efficient production of human monoclonal antibodies from peripheral blood lymphocytes. Hum Antibodies. 2002;11(3):85-96.

Yarmush, M.L. et al., Identification and characterization of rabbit-mouse hybridomas secreting rabbit immunoglobulin chains. Proc Natl Acad Sci U S A. May 1980;77(5):2899-903.

Zhu, Y. et al., Improved fusion partners transfected with DNA fragment encoding IL-11 on generation of human B lymphocyte hybridomas. Hum Antibodies. 1999;9(1):1-7.

Bodnar, A.G. et al., Extension of life-span by introduction of telomerase into normal human cells. Science. Jan. 16, 1998;279(5349):349-52.

Counter, C.M. et al., Telomerase activity is restored in human cells by ectopic expression of hTERT (hEST2), the catalytic subunit of telomerase. Oncogene. Mar. 5, 1998;16(9):1217-22.

Delange, T. Telomeres and senescence: ending the debate. Science. Jan. 16, 1998;279(5349):334-5.

Dickson, M.A. et al., Human keratinocytes that express hTERT and also bypass a p16(INK4a)-enforced mechanism that limits life span become immortal yet retain normal growth and differentiation characteristics. Mol Cell Biol. Feb. 2000;20(4):1436-47.

Greenberg, R.A. Expression of mouse telomerase reverse transcriptase during development, differentiation and proliferation. Oncogene. Apr. 2, 1998;16(13):1723-30.

Ishii, Y. ete al., Telomerase activity in hybrids between telomerase-negative and telomerase-positive immortal human cells in repressed in the different complementation groups but not in the same complementation group of immortality. Mech Ageing Dev. Oct. 22, 1999; 110(3):175-93.

Katoh, M. et al., A repressor function for telomerase activity in telomerase-negative immortal cells. Mol Carcinog. Jan. 1998;21(1):17-25.

Kim, N. and Wu, F. Advances in quantification and characterization of telomerase activity by the telomeric repeat amplification protocol (TRAP). Nucleic Acids Res. Jul. 1, 1997;25(13):2595-7.

Kohler, G. and Milstein, C. Continuous cultures of fused cells secreting antibody of predefined specificity. Nature. Aug. 7, 1975;256(5517):495-7.

Nakamura, T.M. et al., Telomerase catalytic subunit homologs from fission yeast and human. Science. Aug. 15, 1997;277(5328):955-9.

Naviaux, R.K. et al., The pCL vector system: rapid production of helper-free, high-titer, recombinant retroviruses. J Virol. Aug. 1996;70(8):5701-5.

Rheinwald, J.G., et al., "Properties of immortal cell lines arising from human epidermal keratinocytes stably transfected to express hTERT (human telomerase catalytic subunit)," Proceedings of the 90th Annual Meeting of The American Association for Cancer Research, Philapelphia, PA, Apr. 10-14, 1999.

Rufer, N. et al., Transfer of the human telomerase reverse transcriptase (TERT) gene into T lymphocytes results in extension of replicative potential. Blood. Aug. 1, 2001;98(3):597-603.

Weng, N.P. et al., Regulation of telomere length and telomerase in T and B cells: a mechanism for maintaining replicative potential. Immunity. Aug. 1998;9(2):151-7.

Wright, W.E. et al., Experimental elongation of telomeres extends the lifespan of immortal x normal cell hybrids. EMBO J. Apr. 1, 1996;15(7):1734-41.

Ephrussi, B. and Weiss, M.C. Hybrid somatic cells. Sci Am. Apr. 1969;220(4):26-35.

* cited by examiner

SEQUENCE LISTING

<160> NUMBER OF SEQ ID NOS: 8

<210> SEQ ID NO 1
<211> LENGTH: 18
<212> TYPE: DNA
<213> ORGANISM: Mus musculus

<400> SEQUENCE: 1
tgagcggaca aaacatcc                                                   18

<210> SEQ ID NO 2
<211> LENGTH: 20
<212> TYPE: DNA
<213> ORGANISM: Mus musculus

<400> SEQUENCE: 2
aggctcgtct taattgaggt                                                 20

<210> SEQ ID NO 3
<211> LENGTH: 20
<212> TYPE: DNA
<213> ORGANISM: Homo sapiens

<400> SEQUENCE: 3
cggaagagtg tctggagcaa                                                 20

<210> SEQ ID NO 4
<211> LENGTH: 19
<212> TYPE: DNA
<213> ORGANISM: Homo sapiens

<400> SEQUENCE: 4
ggatgaagcg gagtctgga                                                  19

<210> SEQ ID NO 5
<211> LENGTH: 21
<212> TYPE: DNA
<213> ORGANISM: Mus musculus

<400> SEQUENCE: 5
gaccccttca ttgacctcaa c                                               21

<210> SEQ ID NO 6
<211> LENGTH: 20
<212> TYPE: DNA
<213> ORGANISM: Mus musculus

<400> SEQUENCE: 6
cttctccatg gtggtgaaga                                                 20

<210> SEQ ID NO 7
<211> LENGTH: 38
<212> TYPE: DNA
<213> ORGANISM: Homo sapiens

<400> SEQUENCE: 7
cgggatccga agccaccatg aactccttct ccacaagc                             38

<210> SEQ ID NO 8
<211> LENGTH: 36
<212> TYPE: DNA
<213> ORGANISM: Homo sapiens

```
<400> SEQUENCE: 8
cggaattcgt cgagaactac atttgccgaa gagccc                    36
```

FUSION PARTNER CELLS AND USES THEREOF

RELATED APPLICATIONS

This application claims the benefit under 35 U.S.C. §119 of U.S. Provisional Patent Application Nos. 60/341,567, filed Dec. 18, 2001, 60/349,872, filed Jan. 17, 2002, 60/355,236, filed Feb. 7, 2002, and 60/375,236, filed Apr. 24, 2002, the entire contents of which are hereby incorporated by reference.

GOVERNMENT SUPPORT

The invention was supported, in whole or in part, by grant number K08 HL04463-01 from National Institutes of Health. The Government has certain rights in the invention.

BACKGROUND OF THE INVENTION

Antibodies are the effector molecules of the humoral immune response in mammals (B. Alberts et al., *Molecular Biology of the Cell* (Garland Publishing, Inc. 1994); E. Harlow et al., *Antibodies: A Laboratory Manual* (Cold Spring Harbor Laboratory, Cold Spring Harbor, 1988). Also known as immunoglobulins (Ig), they are produced by B-lymphocytes in response to antigen stimulation. Each B-lymphocyte produces an antibody with a defined specificity for a particular antigen. During an infection, an individual will generally produce multiple unique B-lymphocyte clones, each expressing and secreting a single type of antibody directed at an antigen expressed by the infectious organism. Following the resolution of the infection, the newly-generated B-lymphocytes enter a quiescent state characterized by minimal proliferation and antibody secretion. These quiescent B-lymphocytes can last for the lifetime of the individual and serve as an immunological memory that can be quickly tapped should the individual again encounter the same infectious organism.

The development of monoclonal antibody technology in the 1970s greatly facilitated the study of antibody biology and the adaptation of antibodies for use in research and medicine (B. Alberts et al., *Molecular Biology of the Cell* (Garland Publishing, Inc. 1994); G. Kohler et al., *Nature* 256:495 (1975)). Monoclonal antibodies are produced by hybrid cells that result from a fusion between normal B-lymphocytes and myeloma cells. The myeloma cell lines used for fusion are B-lymphocyte tumor cell lines that grow well in vitro and can propagate indefinitely, in contrast to normal B-lymphocytes that cannot replicate or produce antibody in vitro for more than a few days. Cells derived from a fusion of the two types of cells combine the in vitro growth characteristics of the myeloma cell line with the production of an antibody derived from the B-lymphocyte.

Hybrid cells (hybridomas) are generally produced from mass fusions between murine splenocytes, which are highly enriched for B-lymphocytes, and myeloma "fusion partner cells" (B. Alberts et al., *Molecular Biology of the Cell* (Garland Publishing, Inc. 1994); E. Harlow et al., *Antibodies. A Laboratory Manual* (Cold Spring Harbor Laboratory, Cold Spring Harbor, 1988). The cells in the fusion are subsequently distributed into pools that can be analyzed for the production of antibodies with the desired specificity. Pools that test positive can be further subdivided until single cell clones are identified that produce antibodies of the desired specificity. Antibodies produced by such clones are called monoclonal antibodies.

Monoclonal antibodies have many advantages that make them particularly useful in research and medicine. They can be produced in large quantities and often have high and specific affinities for their particular antigens. However, their enormous potential utility is counter-balanced by the difficulty in producing antibodies suitable for pharmaceutical use. This is because the current state of the art for monoclonal antibody production is most effective in the production of murine antibodies. Murine antibodies are recognized by the human immune system as foreign. Patients may have allergic or anaphylactic reactions to the antibodies, or may develop their own antibodies directed against the murine antibodies. This can lead to the formation of large immune complexes that can precipitate in tissues and cause serum sickness, a syndrome consisting of fever, muscle and joint aches, rash, and renal and cerebrovascular injury. Consequently, murine antibodies are of limited value for use in humans.

Many investigators have attempted to generate human monoclonal antibodies by generating hybridomas with human B-lymphocytes (N. Chiorazzi et al, *J. Exp. Med.* 156: 930 (1982); C. M. Croce et al., *Nature* 288:488 (1980); P. A. Edwards et al, *Eur. J. Immunol.* 12:641 (1982); R. Nowinski et al, *Science* 210:537 (1980); L. Olsson et al, *Proc. Natl. Acad. Sci. USA* 77:5429; J. W. Pickering et al, *J. Immunol.* 129:406 (1982)). Unfortunately, hybrid cells exhibit poor growth in vitro, low levels of antibody expression, instability of antibody expression, and a poor ability to be cloned by limiting dilution. The explanation for these phenotypes has not been elucidated. Accordingly, most investigators have concluded that the production of human monoclonal antibodies through the generation of hybrid cells formed with human B-lymphocytes is not feasible.

Consequently, diverse and cumbersome approaches have been used to produce human monoclonal antibodies. These include "humanizing" mouse antibodies by creating hybrid murine/hybrid immunoglobulin genes and generating antibodies in transgenic mice that bear human immunoglobulin gene loci. However, these methods are only able to produce antibodies that have been generated in mice by the murine immune system. They do not allow the isolation, production, and use of the naturally-occurring antibodies, the immunological memory that the human immune system produces in response to infections and other antigen exposures. The ability to make monoclonal antibodies directly from human B-lymphocytes is therefore needed and would be of considerable value.

SUMMARY OF THE INVENTION

The present invention relates in some aspects to a method of making human monoclonal antibodies through the use of novel hybrid cells. In the invention, hybrid cells are created by combining three elements: a fusion partner cell, a fusion cell (in particular a human B-lymphocyte), and one or more ectopic genes that alter the phenotype of the hybrid cells. As described herein, the expression of an ectopic gene in hybrid cells formed from primary human B-lymphocytes and fusion partner cells improves their growth rate, level of Ig expression, stability of Ig expression, and the ability to be cloned by limiting dilution.

The present invention has made it possible to produce human antibody-secreting hybridomas directly from native human B-lymphocytes. Native human antibodies have isotypes and antigen specificities selected by the human immune response for their efficacy against pathogenic organisms and other foreign antigens. Indeed, many antibodies that are made by the human immune system in response to infections are potent enough to provide life-long immunity. Any person who has recovered from an infection is a reservoir of B-cells encoding antibodies that may be useful as therapeutics to protect another individual suffering from the same infection. For the first time, the present invention makes all of those antibodies accessible for use in research and medicine. In addition, the present method for making human antibodies is much less cumbersome than previously available methods.

The present invention is based on a number of novel observations that explain the obstacles that have prevented others from efficiently generating human monoclonal antibody-secreting cells by cell fusion with primary human B-lymphocytes.

According to one aspect of the invention, fusion partner cells are provided. The fusion partner cells include at least two ectopically expressed nucleic acid molecules, wherein each of the ectopically expressed nucleic acid molecules encodes a polypeptide that when expressed in the hybrid cell, alters the phenotype of the hybrid cell. Preferably the phenotypic alteration mediated by the polypeptides is inhibition of cell mortality. In preferred embodiments, the polypeptide is selected from the group consisting of a polypeptide that inhibits tumor suppressor activity, a polypeptide that inhibits apoptosis, a polypeptide that promotes growth, and a polypeptide that enhances cell survival.

In certain of the preferred embodiments, at least one of the two polypeptides is a polypeptide that inhibits apoptosis. In certain embodiments, the polypeptide that inhibits apoptosis is a polypeptide which enhances telomerase activity. Preferably, the polypeptide is a telomerase. More preferably, the telomerase is the human telomerase catalytic subunit (hTERT). In certain other embodiments, the polypeptide that inhibits apoptosis is selected from the group consisting of bcl-2 and bcl-xL.

In other preferred embodiments, one of the at least two polypeptides is a polypeptide that promotes growth. In some embodiments, the polypeptide that promotes growth is selected from the group consisting of interleukin-6 (IL-6), interleukin-11 (IL-11) v-Abl, c-myc and myb. In preferred embodiments, IL-6 is human IL-6.

In other preferred embodiments, one of the at least two polypeptides is a polypeptide that inhibits tumor suppressor activity. In certain embodiments, the polypeptide that inhibits tumor suppressor activity is a polypeptide that inhibits p53 activity. In preferred embodiments, the polypeptide that inhibits p53 activity is selected from the group consisting of p53 dominant negative proteins, SV40 large T antigen, HPV E6, mdm2, and Hdm2. Preferably, the p53 dominant negative protein is a truncated p53 protein. In particularly preferred embodiments, the truncated p53 protein is a C-terminal p53 miniprotein (p53 DD). In other embodiments, the polypeptide that inhibits tumor suppressor activity is a polypeptide that inhibits Rb activity. Preferably, the polypeptide that inhibits Rb activity is selected from the group consisting of Rb dominant negative proteins, SV40 large T antigen, HPV E7, E1a, cdk/cyclin D fusion, IL-6 and mutant cdk4.

In still other preferred embodiments, one of the at least two polypeptides is a polypeptide that enhances cell survival. Preferably, the polypeptide that enhances cell survival is SV40 small T antigen.

In other embodiments, the cell is a mammalian cell. Preferably, the mammalian cell is a human cell or a mouse cell. In some embodiments, the mammalian cell is a myeloma cell.

In certain embodiments, the at least two ectopically expressed nucleic acid molecules are expressed from one or more exogenously introduced expression cassettes. Preferably, the cassettes are included in viral vectors or in plasmid vectors. In some embodiments, the vectors are not integrated in one or more chromosomes. In other embodiments, the cassettes are integrated in one or more chromosomes. In some embodiments, there is more than one cassette, and each cassette includes at least one constitutive promoter operably linked to a nucleic acid molecule. In alternative embodiments, there is more than one cassette, and each cassette includes at least one regulatable promoter operably linked to a nucleic acid molecule.

According to another aspect of the invention, other fusion partner cells are provided. The fusion partner cells include at least one ectopically expressed nucleic acid molecule that regulates the expression of at least one polypeptide that when expressed in the hybrid cell, alters the phenotype of the hybrid cell. In some embodiments, the polypeptide is selected from the group consisting of a polypeptide that inhibits tumor suppressor activity, a polypeptide that inhibits apoptosis, a polypeptide that promotes growth, and a polypeptide that enhances cell survival. In certain embodiments, the ectopically expressed nucleic acid molecules are antisense molecules or dsRNA molecules that inhibit the expression of the polypeptide that when expressed in the hybrid cell, alters the phenotype of the hybrid cell. In some embodiments, the ectopically expressed nucleic acid molecule encodes a molecule that modulates the expression or activity of a polypeptide that when expressed in the hybrid cell, alters the phenotype of the hybrid cell.

According to another aspect of the invention, methods for making any of the fusion partner cells of the foregoing aspects of the invention are provided. The methods include introducing into a cell at least two ectopically expressed nucleic acid molecules, each of which encodes a polypeptide that when expressed in the hybrid cell, alters the phenotype of the hybrid cell. In some embodiments, the nucleic acid molecule is operably linked to a promoter. In certain embodiments, the promoter is constitutively active. In some embodiments, the promoter is regulatable.

According to still another aspect of the invention, fusion partner cells are provided. The fusion partner cells include a soluble or membrane bound growth factor selected from the group consisting of IL-6 and IL-11 and at least one ectopically expressed nucleic acid molecule that encodes at least one polypeptide that when expressed in the hybrid cell, alters the phenotype of the hybrid cell. In some embodiments, the polypeptide is selected from the group consisting of a polypeptide that inhibits tumor suppressor activity, a polypeptide that inhibits apoptosis, a polypeptide that promotes growth, and a polypeptide that enhances cell survival. In certain embodiments, the soluble growth factor is IL-6. In some embodiments, the soluble growth factor is a mutant IL-6.

According to another aspect of the invention methods for making the foregoing fusion partner cells are provided. The methods include introducing into a cell at least one ectopically expressed nucleic acid molecule that encodes at least one polypeptide that when expressed in the hybrid cell, alters the phenotype of the hybrid cell, and culturing the cells in the presence of a soluble growth factor selected from the group consisting of IL-6 and IL-11. In some embodiments, the soluble growth factor is IL-6. In certain embodiments, the nucleic acid molecule is operably linked to a promoter. In some embodiments, the promoter is constitutively active. In some embodiments, the promoter is regulatable.

According to another aspect of the invention, fusion partner cells are provided. The fusion partner cells include an ectopically expressed nucleic acid molecule that encodes a polypeptide that inhibits tumor suppressor activity. In some embodiments, the tumor suppressor activity is p53 activity or Rb activity. Preferably, the polypeptide that inhibits tumor suppressor activity is a p53-inhibiting polypeptide selected from the group consisting of p53 dominant negative proteins, SV40 large T antigen, HPV E6, mdm2 and Hdm2. In some embodiments, the p53 dominant negative protein is a truncated or mutated p53 protein. In preferred embodiments, the truncated p53 protein is a C-terminal p53 miniprotein (p53 DD). In other preferred embodiments, the polypeptide that inhibits tumor suppressor activity is a Rb-inhibiting polypeptide selected from the group consisting of Rb dominant negative proteins, E1a, SV40 large T antigen, HPV E7, cdk/cyclin D fusion, IL-6 and mutant cdk4. Preferably the Rb-inhibiting polypeptide is SV40 large T antigen. In certain of the foregoing embodiments, the cell is a mammalian myeloma cell. Preferably the mammalian myeloma cell is a human myeloma cell or a mouse myeloma cell. In other embodiments, the cell is a non-myeloma cell, preferably a lymphoblastoid cell.

According to another aspect of the invention, methods for making any of the fusion partner cells of the foregoing aspect of the invention are provided. The methods include introducing into a cell a nucleic acid molecule that encodes a polypeptide that inhibits tumor suppressor activity. Preferably, the nucleic acid molecule is operably linked to a promoter. In some embodiments the promoter is constitutively active. In other embodiments the promoter is regulatable. In some embodiments, the nucleic acid molecule encodes a p53-inhibiting polypeptide selected from the group consisting of p53 dominant negative proteins, SV40 large T antigen, HPV E6, mdm2, and Hdm2. In preferred embodiments, the p53 dominant negative protein is a truncated p53 protein and preferably the truncated p53 protein is a C-terminal p53 miniprotein (p53 DD). The polypeptide that inhibits tumor suppressor activity in other embodiments is a Rb-inhibiting polypeptide selected from the group consisting of Rb dominant negative proteins, E1a, SV40 large T antigen, HPV E7 and cdk/cyclin D fusion. The Rb-inhibiting polypeptide preferably is SV40 large T antigen.

According to another aspect of the invention, fusion partner cells are provided. The fusion partner cells include an ectopically expressed nucleic acid molecule that encodes a growth promoting polypeptide, wherein the nucleic acid is derived from a different species than the cell. In some embodiments, the nucleic acid encodes interleukin-6 (IL-6). In certain embodiments, the nucleic acid is encodes non-murine IL-6. In preferred embodiments, the cell is a human cell.

According to a further aspect of the invention, antibody-producing cells are provided. The antibody-producing cells include any of the fusion partner cells of the foregoing aspect of the invention fused to a B lymphocyte.

According to yet another aspect of the invention, human fusion partner cells are provided. The human fusion partner cells include an ectopically expressed nucleic acid molecule that encodes a growth promoting polypeptide, wherein the nucleic acid is derived from a human. In some embodiments, the nucleic acid encodes IL-6.

According to a further aspect of the invention, hybridomas are provided. The hybridomas include any of the aforementioned fusion partner cells of the invention fused to a primary mammalian cell. In some embodiments, the primary mammalian cell is a B lymphocyte. In preferred embodiments, the primary mammalian cell is isolated from peripheral blood. In other embodiments, the primary mammalian cell is a tumor cell, a hematopoietic cell, or a lymphocyte, preferably a T lymphocyte. Preferably, the primary mammalian cell is a human cell. In certain embodiments, the primary mammalian cell is a somatic cell.

In still other embodiments, the B lymphocyte is obtained from an individual, preferably from tissue selected from the group consisting of: peripheral blood, bone marrow, cord blood, lymph nodes, Peyer's patches, spleen, tumor samples, and sites of infection. In certain embodiments, the individual had been previously exposed to an infectious agent or an antigen thereof. Preferably, the infectious agent is selected from the group consisting of viruses, bacteria, fungi, and prions. In other embodiments, the individual is an individual who had been exposed to a tumor or an antigen thereof. The tumor preferably is a solid tumor selected from the group consisting of a gastrointestinal tumor, a breast tumor, a kidney tumor, a brain tumor, a liver tumor, a stomach tumor, a lung tumor, a pancreatic tumor, a tumor of the reproductive systems, a prostate tumor, an eye tumor, a skin tumor, a melanoma, adenomas, polyps, dysplasias, in situ carcinoma, and intra-epithelial neoplasm. In other preferred embodiments, the tumor is a hematopoietic tumor selected from the group consisting of leukemia, lymphoma, myeloma, and myelodysplastic syndromes. In still other embodiments, the individual developed an immune response against a self-antigen.

According to another aspect of the invention, methods for making immunoglobulin-secreting hybrid cells are provided. The methods include fusing B lymphocytes to the fusion partner cells of the foregoing aspects of the invention to form hybrid cells, thereby producing immunoglobulin secreting hybrid cells. In some embodiments, the method also includes cloning the hybrid cells, preferably by limiting dilution. In certain embodiments, the methods also include culturing the hybrid cells in a selective medium that selects against the B lymphocytes and the fusion partner cells. In other embodiments, the methods also include identifying immunoglobulin-secreting hybrid cells in the culture.

The B lymphocytes can be obtained from a mammal, preferably from a human. In other embodiments, the B lymphocytes are obtained from a mouse, cow sheep, pig, goat, rat, or rabbit. In certain embodiments, the mouse expresses a non-mouse immunoglobulin-encoding nucleotide sequence. Preferably, the non-mouse immunoglobulin-encoding nucleotide sequences are human immunoglobulin chromosomal loci or cow immunoglobulin chromosomal loci.

According to another aspect of the invention, a library of immunoglobulin-secreting cells is provided. The library includes hybrid cells produced by the foregoing methods.

According to a further aspect of the invention, methods for making immunoglobulin-secreting hybrid cells are provided. The methods include fusing B lymphocytes to a fusion partner cell comprising at least one ectopically expressed nucleic acid molecule, to form hybrid cells, thereby producing immunoglobulin secreting hybrid cells. The ectopically expressed nucleic acid molecule encodes a polypeptide that when expressed in the hybrid cell, alters the phenotype of the hybrid cell.

In another aspect of the invention, methods for making immunoglobulin-secreting hybrid cells are provided. The methods include fusing B lymphocytes to a fusion partner cell to form immunoglobulin secreting hybrid cells, and ectopically expressing at least one nucleic acid molecule that encodes a polypeptide that when expressed in the hybrid cell, alters the phenotype of the hybrid cell.

According to yet another aspect of the invention, methods for cloning immunoglobulin-encoding nucleotide sequences are provided. The methods include preparing a library of human hybridoma cells, selecting from the library one or more immunoglobulin-secreting cells of interest, and isolating immunoglobulin-encoding nucleotide sequences from the selected immunoglobulin-secreting cells. In some embodiments, the library of human hybridoma cells includes the immunoglobulin-secreting cells of the foregoing aspect of the invention. In other embodiments the human immunoglobulin-secreting cells are selected based on their secretion of an immunoglobulin of interest. Preferably, the selection is performed by an immunoassay of immunoglobulins secreted by the cells of the library. In certain embodiments, the immunoglobulin-encoding nucleotide sequences encode a CDR region.

According to another aspect of the invention, methods for producing an antibody with a desired specificity are provided. The methods include preparing a library of hybridoma pools, performing limiting dilution on the hybridoma pools, analyzing antibody produced by the hybridoma pools to identify a putative antibody with a desired specificity, cloning immunoglobulin genes from hybridoma pools that produce the putative antibody, and expressing the immunoglobulin genes in a host cell to produce an antibody with desired specificity. In some embodiments, the antibody is analyzed to determine a physical characteristic selected from the group consisting of affinity, idiotype, allotype, isotype, and conformation. In certain embodiments, the immunoglobulin genes encode a CDR region. In other embodiments, the immunoglobulin genes encode variable and framework regions. In still other embodiments, the methods also include performing recombinant DNA techniques to a phenocopy of the antibody having desired specificity. The methods also can include cloning the immunoglobulin genes encoding a CDR region into a vector containing generic heavy chain and light chain constant domains. In some embodiments, the hybridoma pools are the library of secreted immunoglobulin secreting hybrid cells of the foregoing aspect of the invention.

According to another aspect of the invention, methods for making immunoglobulin-secreting hybrid cells are provided. The methods include fusing B lymphocytes to a fusion partner cell comprising at least one ectopically expressed nucleic acid molecule, wherein the ectopically expressed nucleic acid molecule encodes a polypeptide that when expressed in the hybrid cell, alters the phenotype of the hybrid cell, to form hybrid cells, thereby producing immunoglobulin secreting hybrid cells.

According to a further aspect of the invention, a library of immunoglobulin-secreting cells is provided. The library includes hybrid cells produced by the method of the foregoing aspect of the invention.

Methods for making immunoglobulin molecules are provided according to another aspect of the invention. The methods include maintaining immunoglobulin secreting hybrid cells of the foregoing aspects of the invention under conditions appropriate for production of immunoglobulin molecules by immunoglobulin secreting hybrid cells, whereby immunoglobulin molecules are produced.

In another aspect of the invention, methods are provided for making immunoglobulin molecules. The methods include fusing B lymphocytes to the fusion partner cells of any of the foregoing aspects of the invention to form hybrid cells, and maintaining resulting hybrid cells under conditions appropriate for production of immunoglobulin molecules by hybrid cells, whereby immunoglobulin molecules are produced by hybrid cells. In some embodiments, the methods also include isolating the immunoglobulin molecules from the culture medium. In certain embodiments, the B lymphocytes are obtained from an individual. In some embodiments, the individual is a mammal. Preferably, the mammal is a human.

In certain preferred embodiments, the immune system of the human was previously exposed to an infectious agent or an antigen thereof. In certain embodiments, the infectious agent is selected from the group consisting of viruses, bacteria, fungi, and prions. In other preferred embodiments, the immune system of the human was previously exposed to a tumor or an antigen thereof. In still other embodiments, the human developed an immune response against a self-antigen. In some embodiments, the human has received a bone marrow transplant. In other embodiments, the mammal is a mouse, preferably one that was previously exposed to an infectious agent or an antigen thereof, or a tumor or an antigen thereof.

According to another aspect of the invention, an isolated immunoglobulin molecule, an antigen-binding fragment thereof or a CDR thereof is provided. The isolated immunoglobulin molecule, is prepared by any of the methods of the foregoing aspect of the invention. In some embodiments, the isolated immunoglobulin molecule also includes a detectable moiety. In some embodiments, the detectable moiety is a radionuclide, an enzyme, a fluorophore or a chromophore.

In other embodiments, the isolated immunoglobulin molecule also includes a toxic moiety. In some embodiments, the toxic moiety is a radionuclide. In certain embodiments, the radionuclide is selected from the group consisting of $^{225}$Ac, $^{211}$At, $^{212}$Bi, $^{213}$Bi, $^{186}$Rh, $^{188}$Rh, $^{177}$Lu, $^{90}$Y, $^{131}$I, $^{67}$Cu, $^{125}$I, $^{123}$I and $^{77}$Br. In other embodiments, the toxic moiety is a toxin. In certain of these embodiments, the toxin is selected from the group consisting of enediynes, such as calicheamicin and esperamicin and chemical toxins such as methotrexate, doxorubicin, melphalan, chlorambucil, ARA-C, vindesine, mitomycin C, cis-platinum, etoposide, bleomycin and 5-fluorouracil. In some embodiments, the antigen-binding fragment is selected from the group consisting of Fab fragments, F(ab')2 fragments, Fd fragments, Fv fragments, dAb fragments and isolated CDRs. In some embodiments, the B lymphocyte was isolated from a human and the immune system of the human was previously exposed to an infectious agent or an antigen thereof. In some embodiments, the B lymphocyte was isolated from a human and the immune system of the human was previously exposed to a tumor or an antigen thereof. In other embodiments, the B lymphocyte was isolated from a human that received a bone marrow transplant.

According to some aspects of the invention, isolated immunoglobulin molecules or fragments thereof are provided. The isolated immunoglobulin molecules or fragments thereof are prepared by the steps of cloning at least a portion of an immunoglobulin gene that encodes a CDR region of an immunoglobulin molecule from any of the hybridomas of foregoing aspects of the invention, or from the library of immunoglobulin-secreting cells of foregoing aspects of the invention, expressing at least the portion of the immunoglobulin gene in a cell, thereby producing an immunoglobulin molecule or fragment thereof. Additional steps in preparing the isolated immunoglobulin molecules or fragments thereof include isolating the immunoglobulin molecule or fragment thereof produced, thereby producing an isolated immunoglobulin molecule or fragment thereof. In some embodiments, a complete immunoglobulin molecule is produced. In certain embodiments, the complete immunoglobulin molecule is a hybrid molecule, wherein the hybrid is a hybrid of a CDR region of the gene cloned from the hybridoma and an immunoglobulin backbone derived from a different source. In some embodiments, the complete immunoglobulin molecule is derived from the gene cloned from the hybridoma. In some embodiments, the CDR region is an antigen-binding region.

According to another aspect of the invention, methods for treating an infectious disease are provided. The methods include administering to an individual in need of such treatment an effective amount of the isolated immunoglobulin molecule, an antigen-binding fragment thereof, or a CDR region thereof of the foregoing aspect of the invention in which the B lymphocyte was isolated from a human and the immune system of the human was previously exposed to an infection agent or an antigen thereof, wherein the infectious disease is caused by the infectious agent, and wherein the isolated immunoglobulin binds the infectious agent or an antigen thereof.

According to another aspect of the invention, methods for treating cancer are provided. The methods include administering to an individual in need of such treatment an effective amount of the isolated immunoglobulin molecule, an antigen-binding fragment thereof or a CDR region thereof of the foregoing aspect of the invention in which the B lymphocyte was isolated from a human and the immune system of the human was previously exposed to a tumor or an antigen thereof, wherein the cancer is caused by the tumor, and wherein the isolated immunoglobulin binds the tumor or an antigen thereof.

According to another aspect of the invention, methods for diagnosing cancer are provided. The methods include administering to an individual suspected of having a tumor the isolated immunoglobulin molecule, an antigen-binding fragment thereof or a CDR region thereof, of the foregoing aspect of the invention in which the B lymphocyte was isolated from a human and the immune system of the human was previously exposed to a tumor or an antigen thereof, is detectably labeled, and wherein the isolated immunoglobulin binds the tumor or an antigen thereof.

In another aspect of the invention, methods for diagnosing cancer are provided. The methods include obtaining a biological sample from an individual suspected of having a tumor, contacting the biological sample with the foregoing isolated immunoglobulin, an antigen-binding fragment thereof or a CDR region thereof, and determining the presence of the antigen recognized by the immunoglobulin, fragment or CDR region. Preferably the immunoglobulin, fragment or CDR region is detectably labeled, or the immunoglobulin, fragment or CDR region is contacted with a detectably labeled antibody.

According to another aspect of the invention, methods for identifying novel tumor antigens are provided. The methods include contacting a tumor sample with the isolated immunoglobulin molecule, an antigen-binding fragment thereof or a CDR region thereof of the foregoing aspect of the invention in which the B lymphocyte was isolated from a human and the immune system of the human was previously exposed to a tumor or an antigen thereof, and identifying an epitope which binds to the immunoglobulin molecule, an antigen-binding fragment thereof or a CDR region thereof, of the foregoing aspect of the invention in which the B lymphocyte was isolated from a human and the immune system of the human was previously exposed to a tumor or an antigen thereof, wherein the epitope is a tumor antigen.

According to another aspect of the invention, methods of identifying an antibody developed in a human in response to exposure of the immune system of the human to an antigen, the method are provided. The methods include the steps of: generating fused cells by mixing together under fusing conditions: human B cells with culturable fusion partner cells; detecting a subset of surviving fused cells which express an antibody that selectively binds the antigen; isolating nucleotide sequences encoding at least the CDRs of the antibody from the subset of surviving fused cells; transfecting nucleotide sequences isolated in (c) into a culturable cell line to produce a plurality of culturable cells expressing antibodies comprising the CDRs; and screening culturable cells produced in (d) to detect an antibody comprising the CDRs which binds to the antigen, thereby identifying an antibody. In some embodiments, the antigen is an antigen of a pathogenic organism, an antigen of a tumor or a self antigen. In other embodiments, the culturable fusion partner cells are any fusion partner cells of the foregoing aspects of the invention. In still embodiments, the subset of surviving fused cells which express an antibody that selectively binds the antigen is detected by immunoassay, preferably an ELISA assay. In certain preferred embodiments, the nucleotide sequences are extracted by polymerase chain reaction.

In some embodiments the hybridomas described herein are derived from cells of different species.

In other embodiments and aspects SP2/0 cells are used to generate hybridomas. In some embodiments the SP2/0 cells express 5× or greater amounts of mIL-6 than known SP2/mIL-6 cell lines. In other embodiments SP2/0 cells that express mIL-6 but are non-adherent to the plastic tissue culture vessels. In yet other embodiments SP2/0 cells that express non-murine, mammalian IL-6 are provided. SP2/0 cells that express ectopic genes that activate intracellular signaling pathways that are activated by an activated IL-6 receptor are also provided.

In other aspects the invention includes a non-SP2/0 cell line of non-human origin expressing an ectopic IL-6.

A hybridoma comprising a fusion partner cell comprising at least one ectopically expressed nucleic acid molecule, wherein each of the ectopically expressed nucleic acid molecule encodes a polypeptide that when expressed in the hybrid cell, alters the phenotype of the hybrid cell fused to a primary mammalian cell, wherein the primary mammalian cell and the fusion partner cell are derived from different species is provided according to other aspects of the invention. In some embodiments the fusion partner cell is an immortal mammalian cell of B lineage selected from the group consisting of myeloma cells and cells derived from myeloma cells. In other embodiments the primary mammalian cell is a B-lymphocyte such as a B-lymphocyte derived from equine peripheral blood or a B-lymphocyte derived from spleen cells.

An immunoglobulin molecule derived from any of the hybridomas described herein is also contemplated.

The use of the foregoing compositions, molecules and agents in the preparation of medicaments also is provided. In preferred embodiments, the medicaments are useful in the treatment of conditions related to hyperproliferative diseases including cancer or infectious diseases including those caused by pathogens or prions.

These and other aspects of the invention will be described in further detail in connection with the detailed description of the invention.

BRIEF DESCRIPTION OF THE DRAWINGS

FIG. 2A shows results of RT-PCR performed similarly to the one described in FIG. 1. The upper panel depicts ectopic hTERT mRNA; the lower panel depicts GAPDH. FIG. 2B shows a Western Blot for the presence of p53 protein and the ectopically expressed DD mutant p53 protein (upper panel), and the v-Abl protein (lower panel). Lane 0, SP2/0 MP-hTERT. Lanes 1, J3; lane 2, J3 DD MIG; lane 3, J3 DD IL-6; lanes 4, J3 TA MIG; lanes 5 J3 TA IL-6.

DETAILED DESCRIPTION OF THE INVENTION

1. Overview of the Invention

Figure 1:
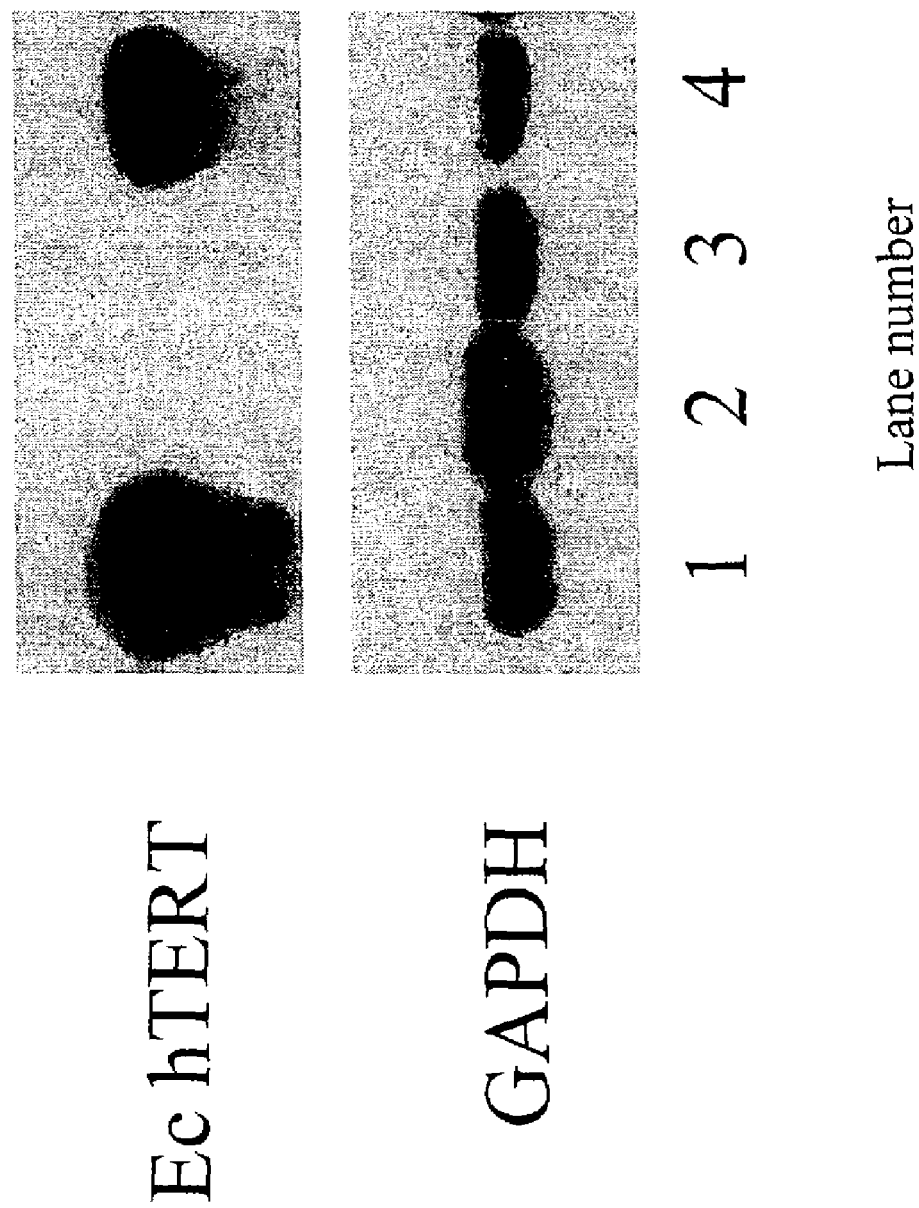
FIG. 1 depicts an assessment of ectopic expression of human telomerase in the cell line SP2/0 mIL-6. Following RT-PCR amplification, ectopic hTERT expression was revealed by a band in the upper panel and GAPDH expression was revealed in the lower panel. GAPDH was assayed as a positive control for the presence of intact RNA. Lane 1, SP2/0 MP-hTERT (positive control for the ectopic hTERT gene). Lane 2, IB4 (a human lymphoblastoid cell line, a negative control for ectopic hTERT). Lane 3, SP2/0 mIL-6 MP (expressing control vector sequences only). Lane 4, SP2/0 MP-hTERT.

It has now been shown that hybrid cells ectopically expressing polypeptides that alter the phenotype of the hybrid cell, particularly those that inhibit cell mortality, have unexpectedly improved growth rates, levels of Ig expression, stability of Ig expression, and ability to be cloned by limiting dilution.

The present invention provides novel fusion partner cells that ectopically express one or more genes that alter the phenotype of a hybrid cell made from a fusion of the fusion partner cell and a fusion cell, hybrid cell lines produced using the fusion partner cells, antibodies produced by certain hybrid cell lines, compositions containing one or a combination of such antibodies or antigen-binding fragments thereof, and methods of using the antibodies or antigen-binding fragments thereof for diagnosis and treatment of diseases characterized by the antigens specifically bound by the antibodies.

2. Scientific Basis for the Present Invention

As described below and in the Examples, Applicants have efficiently generated human monoclonal-antibody-secreting hybrid cells by cell fusion with primary human B-lymphocytes.

As described in Example 1, genes were ectopically expressed in fusion partner cells, specifically human and mouse myeloma cells. Example 2 shows that IL-6 stimulates cloning and antibody production in murine/human hybrid cells. Moreover, as described in Example 3, IL-6 increased the percent of hybrid cell populations that yielded clones secreting high amounts of immunoglobulin. Upon recloning, considerable stability of the immunoglobulin secretion phenotype expressed by hybrid cells expressing mIL-6 was observed.

Example 5 shows that ectopic telomerase (hTERT) expression causes a surprising improvement of improves cloning of murine/human mIL-6 hybrid cell populations. Another unexpected result is shown in Example 6. Although expression of several genes improved growth rates of myeloma cells, coexpression of human IL-6 and v-Abl greatly improved the growth rate of the J3 human myeloma cell lines expressing human telomerase. In addition, ectopic hTERT and IL-6 expression improved the establishment of J3/splenocyte hybrid cells.

Example 8 demonstrated that ectopic expression of a protein that inhibits p53 function in an immortal human fusion partner cell line surprisingly improves the establishment of hybrid cell populations.

Further experiments showed that an IL-6 expressing myeloma cell line effectively formed human immunoglobulin-secreting hybrid cells when fused to human peripheral blood lymphocytes at frequencies that were unexpectedly high.

3. Definitions

The following terms, as used herein, have the following definitions, respectively: The word "antigen" refers to any agent of any form that can induce a B-cell-lineage response and the development of an immunoglobulin with specific binding affinity for the antigen.

The terms "B-cell" and "B-lymphocyte" are used synonymously to refer to B-lineage cells.

The phrase "cell fusion" and the term "fusion" refer to a mixture of fusion partner cells with fusion cells under conditions designed to facilitate the formation of fused cells (hybrid cells).

A "cell line" is a clonal or polyclonal population of cells that will propagate in vitro under appropriate culture conditions.

A "cloned cell line," or "monoclonal cell line," is a cell population in which every cell is an unmodified progeny of a single ancestor cell. A "monoclonal antibody" is an antibody produced by a monoclonal cell line.

The phrase "derived from" is used to denote the origin of the subject under consideration. An antibody that is "derived from human" is an antibody that is encoded at least in part by a human immunoglobulin gene. The term is used synonymously with the terms, "human antibody" and "human immunoglobulin". A "fully human" antibody or immunoglobulin is one that has been produced entirely by genes and cells of human origin. A "fully human" hybrid cell is a cell formed between two human cells, although it may contain elements that are not derived from human but do not affect the nature of the produced antibody, e.g. an ectopic retroviral promoter or a non-human ectopically expressed gene. "Derived from" a particular source is also intended to include entities having substantially the same composition as entities originating from that source. For instance, a synthetic gene would be considered derived from human if it had a sequence similar to a native human gene. For example, a gene is derived from an organism or animal if it has been obtained or isolated from that organism or has the same or substantially the same sequence as the endogenous gene of the organism and has been made or synthesized (e.g., by recombinant DNA methods, synthetic methods).

The phrases "ectopic expression," "ectopically expressed," and "expressed ectopically" refer to gene expression that is under the control of transcription regulatory elements other than those that normally control the endogenous gene at its wild-type chromosomal locus. Also included in the term is expression from an endogenous gene in cases in which a cell has been modified in such a way as to cause or enhance its expression in hybrid cells, including causing the expression of an endogenous gene that would otherwise be transcriptionally silent. This may include altering genetic or epigenetic control mechanisms in the cell in such a way as to subvert the normal regulation of the gene by its endogenous control sequences. One example of this would be to express a protein that would act on the endogenous regulatory sequences of a gene in order to induce expression of the gene.

An "ectopic gene" is a gene that is expressed ectopically. Such genes include exogenous genes that have been introduced into cells, in which they are expressed, and endogenous genes whose expression has been altered in such a manner that it differs from normal expression of the gene in the cell (e.g., its expression has been enhanced, prolonged or increased). "Ectopic expression of a gene" is synonymous with "expression of an ectopic gene" and refers to the expression of a protein from the ectopic gene.

An "endogenous gene" is a gene that exists within the genome of a cell as the cell is obtained.

A "flanked" DNA sequence is one that has nucleotide sequences homologous to a portion of a chromosome on either or both sides of the DNA sequence that permit the DNA sequence to be integrated into the genomic DNA at the homologous portion of the chromosome. The homologous sequences can be immediately adjacent to the DNA to be integrated or separated by DNA sequences that are not homologous provided that they will not prevent homologous recombination from occurring.

The phrase "fusion cell" refers to a cell to be fused with a fusion partner in order to produce a hybrid cell.

The phrases "fusion partner" and "fusion partner cell line" refer to a cell line to be fused with other cells in order to produce hybrid cells. A "fusion partner cell" is a cell of the cell line intended to be fused with another cell in order to produce a hybrid cell.

The phrase "hybrid cell" is used synonymously with "hybridoma," "hybrid," and "fused cell" and refers to a viable cell that is the product of a fusion between a fusion partner cell and fusion cell.

The word "immortal" refers to the ability of a cell or a cell line to be propagated indefinitely when maintained in appropriate culture conditions.

The word "immunoglobulin" is synonymous with the word "antibody." Immunoglobulin is frequently abbreviated as "Ig." The different classes of immunoglobulin molecules include "IgA," "IgD," "IgE," "IgG," and "IgM." IgG includes subclasses IgG1, IgG2, IgG3, and IgG4. Immunoglobulin, as used herein, includes fragments of immunoglobulins.

The phrase "lymphoblastoid cell line" is a B-cell line that either has been infected with the Epstein Barr Virus (EBV) or expresses EBV antigens.

As used herein, a "myeloma" of "myeloma cell" is a cell that is a myeloma cell or is derived from a myeloma cell.

As used herein, a "primary cell" is a cell as removed from an organism without genetic or epigenetic modification. B-cells that have been removed from an organism and treated only with growth promoting agents are still considered to be "primary." The phrase "retroviral gene transfer" refers to the use of RNA viruses to introduce genes into a recipient cell.

The phrase "alters the phenotype" includes enhancing or facilitating any of the following phenotypic properties: the formation of a hybrid cell (e.g., increased production of such cell); proliferation; maintenance or stability of a phenotype of interest (e.g., the ability to express immunoglobulin); ability to survive pro-apoptotic stimuli; and ability to be cloned (e.g., by limiting dilution). Preferably more than one of the foregoing properties is enhanced in the fusion partner cell and/or in a hybrid cell made using the fusion partner cell.

Polypeptides that alter the phenotype, as described herein, include polypeptides that inhibit tumor suppressor activity, polypeptides that inhibit apoptosis, polypeptides that promote growth, and polypeptides that enhance cell survival. As used herein, "polypeptides that inhibit tumor suppressor activity," "polypeptides that inhibit apoptosis," "polypeptides that promote growth," and "polypeptides that enhance cell survival" are polypeptides that modulate (increase or decrease, in time or amount) the one or more of the named biological functions (i.e., tumor suppression, apoptosis, growth promotion, cell survival), including the alteration of cellular pathways that lead to the biological function. It is preferred that the polypeptides that are ectopically expressed to alter the phenotype are from the same species as the fusion partner cell or fusion cell, although polypeptides that retain activity in the fusion partner cell or fusion cell of a different species also may be used.

"Polypeptides that inhibit tumor suppressor activity" include polypeptides that inhibit p53 activity, and polypeptides that inhibit retinoblastoma protein (Rb) activity. Polypeptides that inhibit p53 activity include p53 dominant negative proteins, SV40 large T antigen, HPV E6, mdm2, and Hdm2. p53 dominant negative proteins include truncated p53 proteins, such as C-terminal p53 miniproteins (e.g., p53 DD). Polypeptides that inhibit Rb activity include Rb dominant negative proteins, SV40 large T antigen, HPV E7, E1a, cdk/cyclin D fusion, and mutant cdk4.

"Polypeptides that inhibit apoptosis" include polypeptides that enhance telomerase activity, such as telomerase. "Telomerase" is a protein produced by a telomerase gene. TERT refers to any telomerase-encoding gene; mTERT and hTERT refer to DNA encoding murine and human telomerase respectively. DNA can be genomic DNA, cDNA or synthetic or recombinantly-produced DNA. Polypeptides that inhibit apoptosis also include other apoptosis inhibiting proteins, e.g., bcl-2 and bcl-xL.

"Polypeptides that promote growth" include interleukin-6 (IL-6), interleukin-11 (IL-11) v-Abl, c-myc and myb. In addition, other polypeptides that affect or effect the biological activity of the foregoing polypeptides are included as polypeptides that promote growth. For example, polypeptides that effect IL-6 biological activity that are useful in accordance with the invention include those affecting intracellular processes downstream of IL-6, including constitutively active versions of the IL-6 receptor or its interacting proteins, in particular IL-6R, gp130 and JAK proteins; and proteins that activate STAT proteins, or the GRB2/Ras pathway.

"Polypeptides that enhance cell survival" include, for example, SV40 small T antigen.

As an alternative to ectopic expression of polypeptides, polypeptides that alter the phenotype can be added as isolated polypeptide preparations, or expressed in a feeder layer of cells. For example, IL-6 can be obtained and added to cultures of fusion partner cells, fusion cells, and/or hybrid cells. IL-6 also can be provided ectopically by a feeder cell layer that secretes IL-6 in a culture of fusion partner cells, fusion cells, and/or hybrid cells. Other molecules that are agonists of polypeptide that mediate the phenotypic changes referred to herein, such as a cell-surface receptor molecule, also can be utilized. For example, an IL-6 receptor agonist can be added to cultures of fusion partner cells, fusion cells, and/or hybrid cells to have the same effect as IL-6 itself.

4. Hybrid Cells that Express an Ectopic Telomerase Gene

The present invention relates in some aspects to hybrid cells created by combining three elements: a fusion partner cell, a primary cell, and one or more ectopically expressed genes that when expressed in the hybrid cell, alters the phenotype of the hybrid cell. Hybrid cells created by combining a fusion partner cell derived from a mammalian cell line, a primary human B-lymphocyte, and one or more ectopically expressed genes that when expressed in the hybrid cell, alters the phenotype of the hybrid cell are useful as means of producing human antibodies.

The present invention is based, in part, on the observation that hTERT is not expressed in human/murine hybrid cells. Although human/murine hybrid cells express mTERT, they suffer from inadequate hTERT expression and benefit from the expression of an ectopic hTERT.

The phenotypes of murine/human and human/human hybrid cells created by the presently available methods are very similar (N. Chiorazzi et al, *J. Exp. Med.* 156:930 (1982); C. M. Croce et al., *Nature* 288:488 (1980); P. A. Edwards et al, *Eur. J Immunol.* 12:641 (1982); R. Nowinski et al, *Science* 210:537 (1980); L. Olsson et al, *Proc. Natl. Acad. Sci. USA* 77:5429; J. W. Pickering et al, *J. Immunol.* 129:406 (1982)). Therefore, it is likely that that hybrid cells formed with human fusion partners express hTERT infrequently, not at all, or at sub-optimal levels. This is in accord with the observations of others that human/human hybrid cells formed between TERT-positive and TERT-negative cells are generally TERT-negative (Y. Ishii et al, *Mech. Ageing Dev.* 110:175 (1999); M. Katoh et al, *Mol. Carcinog.* 21:17 (1998); W. E. Wright et al, *Embo. J.* 15:1734 (1996)). Accordingly, hybrid cells formed between fusion partner cells and human primary cells such as B-lymphocytes will also suffer from inadequate hTERT expression. Human/human hybrid cells are specific embodiments of the present invention when provided with ectopic expression of hTERT.

It now has been discovered that the phenotypic properties of hybrid cells can be improved above and beyond improvements made by the expression of hTERT alone, by expression one or more additional genes that favorably alter the phenotype of the hybrid cell. In particular, the genes inhibit a cell mortality phenotype in the hybrid cells. There are, in sum, several different types of genes that can be expressed ectopically in various combinations in the fusion partner cells (i.e., before fusion with a fusion cell) or in the hybrids directly (i.e., after fusion) to increase growth rates, levels of Ig expression, stability of Ig expression, and ability to be cloned by limiting dilution of the hybrid cell. The different types of genes include those that encode polypeptides that inhibit tumor suppressor activity, polypeptides that inhibit apoptosis, polypeptides that promote growth, and polypeptides that enhance cell survival.

a. Fusion Partner Cell Lines

Cell lines suitable for use as fusion partner cell lines in the present invention include mammalian cell lines, such as those of human, murine, or other origin including amphibians, birds, camels, cats, cows, dogs, donkeys, goats, horses, rabbits, rats, sheep, swine, and non-human primates; cell lines of B-lineage, especially myeloma cell lines and lymphoblastoid cell lines; cell lines that are able to grow in vitro; immortal cell lines that express an endogenous telomerase gene; immortal cell lines that express an ectopic telomerase gene; immortal cell lines that do not express a telomerase gene.

b. Fusion Cells (1) Human B-Lineage Cells

In the method of generating hybrid cells that express ectopic genes and secrete immunoglobulins, preferred fusion cells are cells of B-lineage, and in particular primary B-lymphocytes. B-lineage cells can be obtained from living humans with minimal risk and discomfort by phlebotomy or leukopheresis. B-cells can be obtained from the spleen, obtained either at splenectomy or autopsy, and from tonsils removed by tonsillectomy. Furthermore, B-cells can be isolated from lymph nodes obtained at biopsy indicated for the purposes of diagnosis or cancer staging.

In order to make monoclonal antibodies with particular antigenic specificities, B-cells can be obtained from individuals who have been exposed to antigens of interest (antigens against which monoclonal antibodies are to be produced). Specific embodiments of the present invention therefore include forming hybridomas by fusing fusion partners as described herein and B-cells from people who have been or are currently affected by an infectious disease, or who have been immunized or otherwise exposed to components of the infectious agent such as a vaccine. When isolated and purified, such antibodies can be used to provide passive immunity to a person affected with an illness prior to the time when his/her own immune system has generated antibodies.

For instance, in infants the natural decay of maternal antibodies to Haemophilus influenzae engenders a significant risk of contracting meningitis due to the organism. An intravenous infusion of antibody may either reduce the risk of contracting the disease or help to facilitate the recovery of affected infants.

Disease-specific antibodies may also be useful in treating infections that for which there is currently no satisfactory therapy. For example, antibiotics for treating vancomycin-resistant Enterococcus infections are few and of limited efficacy. They may work better when given in conjunction with a specific antibody preparation.

Antibodies of the present invention may be also be useful for patients who lack the ability to effectively make their own antibodies, either due to a specific immunodeficiency syndrome, immunosuppressive medications, general physical deterioration, or the effects of having undergone a bone marrow transplant.

Pathogen-specific antibodies can serve as primary prophylaxis in the event of exposure to a pathogen, such as a virus (e.g., the Human Immunodeficiency Virus (HIV), influenza virus, hepatitis virus) a parasite (e.g., malaria parasite) a bacterium (e.g., salmonella, E. coli) or a fungus (e.g., Candida). For example, administration of antibodies directed at the HIV or a component thereof (e.g. HIV gp41) may be an effective means of preventing the establishment of HIV infection in a person who has been or may become exposed to the virus.

Antibodies made by hybrid cells of the present invention, created with B-cells from individuals who have been exposed to infections or infection-related antigens, will have broad utility. In particular, they will make it possible to passively immunize a person against any antigens by providing him with antibodies directed against the antigens. Hybrid cells that produce such antibodies and the antibodies they produce that bind to such antigens are subjects of this invention.

Further, patients with cancer, including solid tumors and malignant hematological diseases such as leukemia and lymphoma, may develop antibodies against their own malignancies. When isolated and purified, such antibodies may be effective as anti-tumor therapies. Monoclonal antibodies have been shown to be efficacious against some non-Hodgkin's lymphomas and some breast cancers. They can also be useful for the development of diagnostic tests, either detecting the presence of a tumor antigen in the blood of an individual or, through conjugation with a radioactive or other element that allows the antibody to be visualized in the body by radionuclide or other scanning modalities. Hybrid cells of the present invention that bind antigens expressed by malignant cells can be produced by fusing B-cells from patients with cancer with fusion partners. Such hybrid cells and the monoclonal antibodies they produce are specific embodiments of the present invention.

It is also possible to create hybridomas with B-cells from patients with autoimmune diseases syndromes that are associated with the development of auto-antibodies, such as rheumatoid arthritis and systemic lupus erythematosis. The development of such antibodies may be helpful in understanding the pathogenesis of autoimmune diseases and aid the identification of specific auto-antigen binding sites that may serve as useful drug targets. Such hybrid cells and the monoclonal antibodies they produce are further embodiments of this invention.

It may be of interest to generate monoclonal antibody producing cells from individuals who have not had recent exposure to specific antigens, or who have been exposed to only a small amount of antigen, and may therefore possess relatively few B-cells with the desired antigen specificity. In order to increase the proportion of B-cells in such a population that have the desired specificity proliferation of B-cells can be stimulated in vitro in the presence of the desired antigen. Hybrid cells formed with B-cells stimulated with specific antigens and the antibodies they produce are specific embodiments of the present invention.

(2) Non-Human B-Lineage Cells

Many potentially useful antibodies may be difficult to obtain due to the ethical problem of immunizing humans with antigens that may pose them harm. For instance, it would be difficult to generate human monoclonal antibodies as a specific antidote for neurotoxins such as Sarin, because it would be unethical to inoculate a human with neurotoxin-related antigens. Some non-human primates may generate antibodies sufficiently similar to human antibodies that the antibodies would not be detected as foreign by the human immune system. Such primates can be inoculated with the neurotoxin antigens. In an embodiment of the present invention, B-lymphocytes from the inoculated animals are fused to fusion partners in order to create hybrid cells that produce antibodies that bind to the neurotoxin antigens. Such antibodies can be used as an antidote for the toxin. If non-human primates prove to produce antibodies that are compatible with the human immune system the ability to make medically useful antibodies using the present invention will be greatly enhanced.

The present invention is also useful to produce antibodies against a drug that is toxic if over-dosed and not inherently immunogenic by itself. Two examples are acetaminophen and digoxin. A non-human primate can be immunized with these drugs in an immunogenic form, such as conjugated to a hapten and mixed with Freund's Adjuvant. Following a course of immunization, the animal's B-cells could be used within the scope of the present invention to produce hybrid cells that generate antibodies directed against the drug antigens. Such antibodies could be used as an antidote to overdose of the drugs.

The ability to make monoclonal antibodies from non-human animals makes it possible to develop veterinary therapeutics. For these reasons, the present invention can be used to form monoclonal antibody-secreting hybrid cells with B-cells from non-human mammals, pets, or other animals of commercial or other interest. Antibody-secreting hybrid cells can be produced using B-cells from mammals, pets, and other animals such as fish, birds, camels, cats, cows, dogs, donkeys, goats, horses, mice, rabbits, rats, sheep, swine, crustaceans, and non-human primates.

c. Genes

A wide variety of genes (DNA encoding functional polypeptides) can be used to produce hybrid cells that ectopically express the genes.

Any combination of genes (wild-type, mutated, truncated or otherwise altered) can be used that, when expressed ectopically in hybrid cells, facilitates the production of hybrid cells that produce antibodies.

For example, any gene of combination of genes (wild-type, mutated, truncated or otherwise altered) can be used that, when expressed in the hybrid cells, confers upon the hybrid cells one or more phenotypic features selected from the following: improved rate of growth; improved quantity of Ig expression by hybrid cells; improved stability of Ig expression; improved ability to be cloned by limiting dilution. For example, telomerase genes from humans, mice, non-human primates, non-primate mammals, or other organisms can be used in combination with at least one other gene. Specifically, a telomerase gene derived from an organism selected from the group consisting of humans, amphibians, birds, camels, cats, cows, dogs, donkeys, goats, horses, mice, rabbits, rats, sheep, swine, non-human primates, crustaceans, protozoa and yeasts can be used. Particularly preferred telomerase genes are human and non-human primate telomerase genes.

As the term is used herein, a gene is derived from an organism or animal if it has been obtained or isolated from that organism or has the same or substantially the same sequence as the endogenous gene of the organism and has been made or synthesized (e.g., by recombinant DNA methods, synthetic methods). For example, a gene derived from a human can be obtained from a human cell or can be produced to have the same or substantially the same sequence as the human gene (e.g., hTERT). In a specific embodiment, the human telomerase gene is used.

d. Ectopic Expression of Genes

A variety of methods can be used to cause the ectopic expression of genes in hybrid cells. For example, DNA encoding a polypeptide can be introduced into hybrid cells by a variety of methods. An ectopic gene can be introduced at any time in the process of cell fusion. It can be introduced into the fusion cells or the fusion partner cell line prior to fusion. It can be introduced into the hybrid cells as they form during the cell fusion, or it can be introduced into the hybrid cells after they have been formed by cell fusion.

In a particular embodiment, ectopic genes are introduced into a fusion cell line prior to its use in the creation of hybrid cells. Applicants have shown this to be an efficacious and efficient means of introducing an ectopic gene into hybrid cells.

Methods for introducing a gene into the hybrid cells or into cells prior to or during cell fusion include the following: introducing DNA in plasmid vectors or other appropriate constructs into the cells using transfection (with calcium phosphate, proprietary lipid-compounds, or other methods), electroporation, microprojectile bombardment and any other method by which DNA can be introduced into cells; or by using RNA or DNA viruses, such as retroviral vectors and adenoviral vectors, to infect the cells. A gene that has been introduced by these or other methods is an ectopic gene and its expression would constitute ectopic expression of the encoded polypeptide. Within the hybrid cell the gene(s) can exist as an integrated provirus, or in DNA that exists independent of the primary genome of the cell, such as in an episome or in a double minute chromosome.

Retroviral gene transfer is particularly useful to introduce DNA into a fusion partner cell line to produce a fusion partner cell line in which telomerase is ectopically expressed.

The present invention relates to methods and DNA constructs to provide a hybrid cell with ectopic genes that are in such a form that they will be expressed in the hybrid cell, for instance, in a DNA construct containing DNA sequences that cause gene expression. Such sequences may be an enhancer element, a promoter element, or both an enhancer element and a promoter element. The enhancer element(s) can be from a wide variety of sources, including, but not limited to, viral enhancers, eukaryotic enhancers, prokaryotic enhancers and synthetic enhancers. The same is true of the promoter element(s), which can be a viral promoter, an eukaryotic promoter, a prokaryotic promoter or a synthetic promoter. Examples of such sequences include retroviral LTR sequences or the phosphoglycerate kinase (PGK) promoter.

Cells that have acquired and express an ectopic gene can be identified by single cell cloning and analyzing the cloned cells for the presence of ectopic mRNA using RT-PCR with primers specific for the ectopic gene.

Also the subject of this invention are methods and DNA constructs to replace, counteract, or inhibit the effect of DNA sequences that repress or fail to activate the expression of the endogenous telomerase gene. Lack of expression of the endogenous telomerase gene is likely to be mediated by such DNA sequences; therefore, constructs of the present invention are useful to overcome the effects of these DNA sequences and cause expression of the endogenous telomerase gene in hybrid cells. For instance, DNA sequences that prevent telomerase gene expression in the hybrid cells are replaced with DNA sequences that are permissive of telomerase gene expression. Such sequences may be an enhancer element, a promoter element, or both an enhancer element and a promoter element. The enhancer element can be from a wide variety of sources, including, but not limited to, viral enhancers, eukaryotic enhancers, prokaryotic enhancers and synthetic enhancers. The same is true of the promoter element, which can be a viral promoter, an eukaryotic promoter, a prokaryotic promoter or a synthetic promoter. Examples of such sequences include retroviral LTR sequences or the phosphoglycerate kinase (PGK) promoter. An endogenous telomerase gene (or any other gene) that has been modified such that it is expressed in hybrid cells is an ectopic telomerase gene (or any other gene). Expression of such genes constitutes ectopic expression and is an embodiment of the present invention.

Cells that have undergone alteration of their DNA in order to cause such ectopic expression can be identified by single cell cloning and analyzing genomic DNA of the cloned cells for the presence of the altered DNA sequences using PCR with primers specific for the altered DNA sequences.

In another embodiment, a gene is inserted by homologous recombination or other methods into a site within the genome that would ensure its expression in hybrid cells. For example, DNA that is sufficiently homologous to the murine rosa or GAPDH locus can be used to mediate insertion of a gene at those sites. Such a gene is an ectopic gene and its expression would constitute ectopic expression of the polypeptide encoded by the gene. A wide variety of methods to mediate such an insertion into the genome of mammalian cells are known to those of skill in the art.

Cells that have integrated an ectopic gene into the genome of a cell can be identified by single cell cloning and analyzing genomic DNA of the cloned cells for the presence of the ectopic telomerase gene using PCR with primers specific for the altered DNA sequences. Expression of the ectopic gene can be confirmed with RT-PCR.

The c-myc oncogene, NFκB, and the estrogen receptor have been shown to be potent activators of telomerase expression, and p53 and Mad protein expression have been associated with transcriptional repression of the telomerase gene. Enforcing hTERT expression through the ectopic expression of hTERT transcriptional activators such as c-myc, NFκB, and the estrogen receptor or through inhibitors of hTERT transcriptional repressors such as Mad and p53 fall under the definition of ectopic TERT expression as used herein and are specific embodiments of the present invention. Similar manipulations of activators and/or repressors of the other ectopically expressed genes described herein is also included in the invention.

Cells that ectopically express regulators of gene transcription can be identified by single cell cloning and analyzing protein or mRNA of the cloned cells for the presence of the products of the ectopically expressed regulators using Western Blotting or RT-PCR. Expression of the ectopic gene can be confirmed with RT-PCR.

Gene-containing and gene-regulating gene constructs may also contain genes for selectable markers (products that permit identification of cells of interest, such as antibiotic resistance genes and chromogens) in order to identify cells that have taken up the ectopic gene. If the selectable marker gene encodes antibiotic resistance (e.g., puromycin or G418 resistance), cells that have not taken up the ectopic gene do not grow in the presence of the antibiotic. Genes encoding chromogens such as Green Fluorescent Protein (GFP), Blue Fluorescent Protein (BFP), Red Fluorescent Protein (RFP), Yellow Fluorescent Protein (YFP) and beta-galactosidase can serve a similar role. Cells that have taken up the ectopic gene can be selected on the basis of their expression of the chromogen.

In an embodiment, a DNA construct comprises sequences homologous to the endogenous gene promoter that flank sequences of a constitutively active promoter, such as the PGK promoter. Such a construct can also contain a selectable marker gene, such as the gene that confers resistance to the antibiotic puromycin, to facilitate identification of cells that incorporate the DNA construct. The DNA construct can be, for example, a plasmid or a viral vector and the DNA can be linear or circular in configuration. The homologous sequences in the DNA construct facilitate recombination in the gene promoter, replacing DNA sequences that mediate transcriptional repression with DNA sequences that activate gene expression in hybrid cells. The construct can also include further components, such as a plasmid backbone or selectable marker(s). The identification of successful recombinant cells can be facilitated by culturing cells with an antibiotic such as puromycin; non-recombinant cells do not survive in the presence of the antibiotic. In hybrid cells that have undergone such a modification of their endogenous regulatory sequences the PGK promoter directs ectopic expression of the endogenous gene; such a gene comprises an ectopic gene. A hybrid cell possessing such an ectopic gene and the DNA constructs used to create such a hybrid cell are specific embodiments of the present invention.

In another embodiment, a DNA construct comprises sequences that are homologous to chromosomal DNA that is transcriptionally active in hybrid cells flanking a cDNA. Such a construct can also contain a selectable marker gene, such as the gene that confers resistance to the antibiotic puromycin, to facilitate identification of cells that incorporate the DNA construct. The DNA construct can be, for example, a plasmid or a viral vector and the DNA can be linear or circular in configuration. The homologous sequences in the DNA construct facilitate recombination with the chromosomal DNA, thus incorporating the cDNA into a chromosomal region that directs gene expression in hybrid cells. The construct can also include further components, such as a plasmid backbone or selectable marker(s).

The identification of successful recombinant cells can be facilitated by culturing cells with an antibiotic such as puromycin; non-recombinant cells do not survive in the presence of the antibiotic. In hybrid cells that have undergone such a modification the ectopic expression of the gene is determined by chromosomal DNA sequences that flank the ectopic cDNA; such a gene is an ectopic gene. A hybrid cell possessing such an ectopic gene and the DNA constructs used to create such a cell are specific embodiments of the present invention.

e. A Method of Producing Hybrid Cells that Express an Ectopic Telomerase Gene

The present invention relates to a method of producing a hybridoma, comprising fusing a mammalian cell line cell with a fusion cell, under conditions appropriate for production of hybridomas, thereby producing a hybridoma, combined with the introduction of one or more ectopic genes. Methods and conditions for producing hybridomas are well known to those of skill in the art and are routine. They are described, for example, in a published laboratory manual (E. Harlow et al, *Antibodies: A Laboratory Manual* (Cold Spring Harbor Laboratory, Cold Spring Harbor, 1998). The genes are of human or other origin and can be introduced before fusion (into the fusion partner cell or the fusion cell), during fusion, or after fusion into the newly formed hybrid cell. The genes are ectopic and capable of expression in the hybrid cells. As described above, the fusion partner cell line used can be, for example, a human cell line or a murine cell line (e.g., a myeloma cell line) and the fusion cell can be a human B-cell or a non-human B-cell, as would exist in an antigen- or mitogen-stimulated human peripheral blood mononuclear cell population. As described above in the context of the cell lines and the introduction of an ectopic telomerase gene, at least one selectable marker gene or at least one gene that encodes a chromogenic protein can be expressed, but is not required. Hybridomas produced by these methods are also the subject of this invention.

f. A Method of Producing Antibodies

Also the subject of this invention is a method of producing monoclonal antibodies that comprises: fusing a fusion partner cell with a fusion cell, under conditions appropriate for hybridoma formation, wherein the fusion cell is a B-lineage cell; introducing one or more ectopic genes into one of the cells before, during, or after the fusion process, thereby producing hybridomas that ectopically express genes that alter phenotype of the hybrid cell; and maintaining the hybrid cells under conditions appropriate for production of antibodies by the hybridomas, whereby antibodies are produced. Methods and conditions for producing hybridomas and maintaining the hybridomas in order for them to produce monoclonal antibodies are well known to those of skill in the art. Hybridomas of the present invention ectopically express one more genes that encode a polypeptide that inhibits tumor suppressor activity, a polypeptide that inhibits apoptosis, a polypeptide that promotes growth, and/or a polypeptide that enhances cell survival. Hybridomas can be, for example, of murine, human, or of combined murine/human origin.

One of the features of the invention is the ability to generate cell fusions at higher frequencies than previously possible. This is particularly advantageous for cells that do not form fusions with high frequency, such as human/human hybridomas, because the higher frequencies permitted by the invention allow these types of fusions to be performed routinely, as is presently the case for mouse/mouse hybridoma fusions.

There are several ways to measure the increase in fusion frequency that is enabled by the invention. First, fusion frequency can be measured by examining the total number of hybrid cell clones generated using the methods of the invention, as compared to fusions performed using standard methods of cell fusion. Second, one can measure the number of fusion cells or fusion partner cells required to generate a given number of hybrid cell clones. Third, the success rate of fusions in generating hybrid cell clones can be measured. Fourth, one can measure the number or percentage of fusion cells (e.g., human B cells) forming hybrid cells from which immunoglobulin-encoding (preferably CDR-encoding) DNA can be retrieved using the process of the invention. Other measures of fusion frequency, known to one of ordinary skill in the art, also may be used to determine the increase in fusion frequency made possible by application of the present invention.

Human/human fusions tend to give hybrids at a rate of 1 hybrid in $10^6$-$10^8$ lymphocytes (Edwards et al., Eur. J. Immunol. 12(8):641-648, 1982). For the SKO-007 J3 cell line used herein, typically only 10-50% of fusions produce any hybrids at all (Olsson et al., J. Immunol. Methods. 61(1):17-32, 1983). More recently, another example of a human cell line produced hybrid cell colonies at a fusion frequencies approaching 1 per $10^5$ (Karpas et al., Proc. Nat'l. Acad. Sci. USA. 98(4):1799-1804, 2001). These colonies, however, are evident only after 5-6 weeks of culture post-fusion. In contrast, as demonstrated in the Examples below, the methods of the invention provide hybrid cell colonies that are evident at 2 weeks post-fusion.

Thus the invention provides methods for making cell hybrids at fusion frequencies of greater than about 1 in $10^5$, preferably greater than about 2 in $10^5$, more preferably greater than about 5 in $10^5$, more preferably greater than about 1 in $10^4$ still more preferably greater than about 2 in $10^4$, still more preferably greater than about 5 in $10^4$ and yet more preferably greater than about 1 in $10^3$. These frequencies are applicable to fusions of any fusion cell type (e.g., B cells, T cells, dendritic cells, macrophages) and any fusion partner cell type as described herein. The frequencies are applicable to any species' fusion cells and fusion partner cells, or combination of species' fusion cells and fusion partner cells; preferably both the fusion cells and fusion partner cells are human. The invention also includes methods for making cell hybrids in which the hybrids (or colonies thereof) can be identified, isolated and/or cloned in fewer than 5 weeks, preferably fewer than 4 weeks, more preferably fewer than 3 weeks, still more preferably fewer than 2 weeks, and most preferably fewer than 1 week.

The invention also relates to a method of producing human antibodies, comprising: (a) fusing a fusion partner cell with a human B-lineage cell, under conditions appropriate for hybridoma formation (b) introduction of one or more ectopic genes that alter cell phenotype before, during, or after the fusion process (c) thereby producing hybridomas that ectopically express one or more genes that alter cell phenotype and (d) maintaining hybridomas produced in (a) under conditions appropriate for production of antibodies by the hybridomas, whereby human antibodies are produced. Hybridomas of the present invention ectopically express one or more genes that alter cell phenotype. Hybridomas can be, for example, of murine, human, or of combined murine/human origin. Antibodies produced by this method are derived in full or in part from the human B-lineage cell and will therefore be human antibodies. Antibodies produced by this method wherein the fusion partner and the fusion cell are of human origin are fully human antibodies as defined herein.

g. Methods of Producing Human Antibodies of Interest

In one embodiment, this invention is a method of producing a hybridoma that produces antibodies that bind antigens exposed to the immune system of a human. The method comprises producing hybrid cells that ectopically express one or more genes that alter cell phenotype and produce antibodies that bind to antigens, by fusing a fusion partner cell that ectopically expresses one or more genes that alter cell phenotype with a fusion cell of B-lineage derived from a human whose immune system was exposed to the antigen, under conditions appropriate for formation of hybridomas, whereby a hybridoma that expresses an ectopic gene(s) that alter cell phenotype and produces antibodies that bind antigens is produced. Alternatively, one or more ectopic genes that alter cell phenotype can be introduced in the fusion cell prior to fusion, or can be introduced into the hybrid cell during or after the formation of the hybrid cell.

In certain embodiments, the antigen is expressed by a malignant cell. In these embodiments, the human immune system was exposed to the antigen affected by a malignant disease, and the hybridoma produces antibodies that bind antigens expressed by the malignant cell. The malignant cell can be, for example, a cell from a solid malignant tumor or a hematopoietic tumor. The solid tumor can be, for example, a gastrointestinal tumor, a breast tumor, a kidney tumor, a brain tumor, a liver tumor, a stomach tumor, a lung tumor, a pancreatic tumor, a tumor of the reproductive systems, a prostate tumor, an eye tumor, a skin tumor, a melanoma, adenomas, or pre-malignant lesions such as adenomas, polyps, dysplasias, in situ carcinomas, and intra-epithelial neoplasms. The hematopoietic tumor can be, for example, a leukemia, lymphoma, or myeloma, or pre-malignant conditions such as myelodysplastic syndromes.

In another embodiment, the antigen is expressed by a pathogen. In these embodiments, the human immune system was exposed to the antigen of the pathogen, and the hybridoma produces antibodies that bind antigens expressed by the pathogen. The pathogens against which antibodies are produced by the present method include, but are not limited to, RNA viruses, DNA viruses, bacteria, intracellular parasites, fungi, helminths and protozoa.

RNA viruses against which antibodies can be produced by the present method include, but are not limited to, members of RNA virus families such as Picornaviridae, Calciviridae, Togaviridae, Flaviviridae, Coronaviridae, Rhabdoviridae, Filoviridae, Paramyxoviridae, Orthomyxoviridae, Bunyaviridae, Arenaviridae, Reoviridae and Retroviridae. DNA viruses against which antibodies can be produced by the present method include, but are not limited to, members of DNA virus families such as Hepadnaviridae, Parvoviridae, Papovaviridae, Adenoviridae, Herpesviridae and Poxviridae and Hepatitis.

Bacteria against which antibodies can be produced by the present method include, but are not limited to, gram-positive cocci, gram positive bacilli, gram-negative bacteria, anaerobic bacteria, organisms of the families Actinomycetaceae, Bacillaceae, Bartonellaceae, Bordetellae, Captophagaceae, Corynebacteriaceae, Enterobacteriaceae, Legionellaceae, Micrococcaceae, Mycobacteriaceae, Nocardiaceae, Pasteurellaceae, Pseudomonadaceae, Spirochaetaceae, Vibrionaceae and organisms of the genera *Acinetobacter, Brucella, Campylobacter, Erysipelothrix, Ewingella, Francisella, Gardnerella, Helicobacter, Levinea, Listeria, Streptobacillus* and *Tropheryma*.

Intracellular parasites against which antibodies can be produced by the present method include, but are not limited to, Chlamydiaceae, Mycoplasmataceae, Acholeplasmataceae, Rickettsiae and organisms of the genera *Coxiella* and *Ehrlichia*. The fungi are selected from the group consisting of: *Aspergillus, Blastomyces, Candida, Coccidioides, Cryptococcus, Histoplasma, Paracoccicioides, Sporothrix*, organisms of the order Mucorales, organisms inducing choromycosis and mycetoma and organisms of the genera *Trichophyton, Microsporum, Epidermophyton,* and *Malassezia*. The helminths are selected from the group consisting of: Nematodes, Trematodes or Cestodes.

In another embodiment, the antigen is an antigen such as those in venoms, allergens and other molecules introduced by bites, scratches or other contacts with insects or other animals (e.g., snakes, scorpions, frogs, wasps, bees, mosquitoes, spiders, jellyfish, anemones).

In another embodiment, the antigen is a self-antigen, such as from a mammal (e.g., human) who has been or is affected by an autoimmune disease. The self-antigens may be a protein, DNA, RNA, lipid, carbohydrate or other biological molecule.

In a further embodiment, the antigen is a prion antigen, such as from a mammal (e.g., human) who has been or is affected by a prion disease (e.g. Creutzfeld-Jacob Disease, kuru, scrapie, bovine spongiform encephalopathy).

A further embodiment of the present invention is a method of producing hybrid cells in which the fusion cells are mammalian (e.g. human) B-cells stimulated in vitro in the presence of antigens, including but not limited to, proteins, carbohydrates, nucleic acids, organic compounds, and inorganic compounds for the purpose of creating hybrid cells that produce immunoglobulin proteins that are reactive with the stimulating or other antigens.

A further embodiment of the present invention is a method of producing hybrid cells in which the fusion cells are mammalian (e.g. human) B-cells stimulated in vitro in the presence of antigen preparations derived from living organisms, including but not limited to single cells organisms and multicellular organisms and products produced by those organisms, for the purpose of creating hybrid cells that produce immunoglobulin proteins that are reactive with the stimulating or other antigens.

5. Fusion Partner Cell Lines that Express an Ectopic Gene

In the process of creating hybrid cells that express one or more ectopic genes, the ectopic gene(s) can be introduced before, during, or after the process of cell fusion. In one embodiment, an ectopic gene(s) is introduced into an immortal fusion cell line prior to its use in the creation of hybrid cells.

The present invention comprises fusion partners that ectopically express genes that alter the phenotype of the hybrid cell, and their use in fusions with fusion cells to produce hybrid cells that express an ectopic gene(s), and produce antibodies to antigens of interest.

Prior to the work described herein, it was not recognized that ectopic expression of certain phenotype-altering gene(s) in an immortal cell line would improve its ability to serve as a fusion partner cell line in fusions with fusion cells. Therefore, any cell line from any tissue or species of origin that expresses ectopic gene(s) that selectively alter the phenotype of the fusion cells, the fusion partner cells, or the hybrid cells produced therefrom can be used in the method of the present invention to produce hybrid cells. The resulting hybrid cells and products produced by the cells are the subject of the present invention.

The present invention encompasses immortal mammalian cell lines that ectopically express phenotype altering gene(s) and are useful as fusion partner cell lines to produce hybrid cells (hybridomas) in which the gene(s) are ectopically expressed; hybrid cells in which gene(s) are ectopically expressed; antibodies produced by the hybrid cells; DNA constructs useful for producing immortal mammalian cell lines of the present invention and methods of making and using each of the foregoing. In specific embodiments, the cell line is of human or murine origin. The term "a mammalian cell line that ectopically expresses gene(s)" includes cell lines/cells that have themselves been modified, as well as progeny and derivatives thereof.

Prior to the work described herein, it was not recognized that ectopic expression of certain genes or combinations of genes in an immortal cell line would be useful or improve the ability of cells to serve as fusion partners. Therefore, any immortal cell line from any tissue or species of origin, including those cells that express an ectopic telomerase gene and/or an endogenous telomerase gene, is intended for use to produce hybrid cells.

The present invention encompasses immortal mammalian cell lines that ectopically express one or more phenotype-altering genes, preferably in addition to an endogenous telomerase gene (also referred to as mammalian cell lines that have been modified to ectopically express genes) and their use as fusion partner cell lines to produce hybrid cells (e.g., hybridomas) in which the genes that alter phenotype of the hybrid cells are ectopically expressed; hybrid cells in which genes are ectopically expressed; antibodies produced by such hybrid cells; DNA constructs useful for producing mammalian cell lines of the present invention and methods of making and using each of the foregoing. In specific embodiments, the immortal cell line is of human or murine origin. The term "an immortal mammalian cell line that ectopically expresses genes that alter phenotype" includes cell lines/cells that have themselves been modified, as well as progeny and derivatives thereof.

In certain embodiments, two or more genes are ectopically expressed in a cell (e.g., 2, 3, 4, 5 genes, and so on). The invention includes embodiments in which a particular gene is ectopically expressed, while the endogenous copy or copies of that gene is/are mutated or silenced. As an example, telomerase can be ectopically expressed along with another phenotype-altering gene in a cell. Once a cell that expresses an endogenous telomerase gene has been engineered to express telomerase from an ectopic gene, there may be little or no additional benefit resulting from expression of the endogenous telomerase gene. Therefore, an embodiment of the present invention is an immortal mammalian cell that expresses telomerase from an endogenous gene, is subsequently modified to express an ectopic telomerase gene (and at least one other gene that alters the phenotype of the cell), and then is modified or undergoes a change(s) (e.g., during culturing) such that the endogenous gene is no longer expressed or is expressed at lower levels.

Thus in the foregoing example, the present invention encompasses immortal mammalian cell lines that formerly ectopically expressed telomerase in addition to an endogenous telomerase gene, but have subsequently been modified or have undergone spontaneous change so that they no longer express the endogenous telomerase gene, and their use as fusion partner cell lines to produce hybrid cells (hybridomas) in which telomerase is ectopically expressed; hybrid cells in which endogenous telomerase is not expressed or is expressed at a lower level than the level at which it was expressed formerly and telomerase is ectopically expressed; antibodies produced by such hybrid cells; DNA constructs useful for producing immortal mammalian cell lines of the present invention and methods of making and using each of the foregoing. In specific embodiments, the cell line is of human or murine origin. The term "an immortal mammalian cell line that formerly ectopically expressed a gene in addition to an endogenous copy of that gene, but have subsequently been modified to that they no longer express the endogenous gene" includes cell lines/cells that have themselves been modified, as well as progeny and derivatives thereof.

This principle applies to other ectopically expressed genes. For example, one can alter a cell to advantageously reduce the expression of a gene that counteracts the effect of an ectopically expressed gene. As an example of this, in certain embodiments of the invention IL-6 polypeptide is expressed or added to cells. One can enhance the effect of IL-6 by reducing the expression of receptors for other growth factors that tend to counteract IL-6 effects, such as IL-4 or IL-10.

In all of these embodiments, the telomerase gene can be derived from an organism selected from a wide variety of organisms, including, but not limited to, humans, amphibians, birds, camels, cats, cows, dogs, donkeys, goats, horses, mice, rabbits, rats, sheep, swine, non-human primates, protozoa, crustaceans and yeasts.

Specific embodiments of this invention are immortal human B-lineage fusion partner cell lines that express one or more tumor suppressor inhibiting polypeptides, or combinations of genes that alter the phenotype of the fusion partner cell or hybrids made therefrom. In one embodiment, an ectopic hTERT is expressed with one or more other genes that alter phenotype, such as polypeptides that inhibit tumor suppressor activity, polypeptides that inhibit apoptosis, polypeptides that promote growth, and polypeptides that enhance cell survival. Other specific embodiments include ectopic expression of hTERT with IL-6, and optionally including other genes that alter the phenotype of the cell or hybrids made therefrom.

Still other embodiments provide fusion partner cells in which a polypeptide that inhibits tumor suppressor activity, such as a p53 dominant negative polypeptide, is ectopically expressed. In these embodiments, one or more additional genes that alter phenotype can be expressed in conjunction with the ectopically expressed polypeptide that inhibits tumor suppressor activity. Also included are the use of the foregoing cells in fusions with primary human B-lymphocytes to produce fully human hybrid cells in which telomerase is ectopically expressed; fully human hybrid cells in which the gene(s) is/are ectopically expressed; and fully human antibodies produced by the hybrid cells.

The immortal mammalian cell line, in the specific embodiments described above, has been modified to ectopically express one or more genes from DNA sequences permissive of expression in hybrid cells. The sequences may include, for example, an enhancer element, a promoter element, or both an enhancer element and a promoter element. The enhancer element can be from a wide variety of sources, including, but not limited to, viral enhancers, eukaryotic enhancers, prokaryotic enhancers and synthetic enhancers. The same is true of the promoter element, which can be a viral promoter, an eukaryotic promoter, a prokaryotic promoter or a synthetic promoter (a non-naturally occurring or designed promoter).

In another embodiment, genomic DNA sequences in the immortal mammalian cell line that regulate an endogenous gene are altered to increase, prolong or enhance expression of an endogenous gene in hybrid cells, resulting in ectopic expression of the gene as defined herein. Alternatively, a gene is incorporated in the genome of the cell line at a site such that the gene is under the control of transcriptional regulatory elements that direct expression of the gene in hybrid cells. Finally, an endogenous gene can be constitutively expressed as a result of the constitutive expression of a transcriptional activator of gene expression, or due to the inactivation of inhibitors of gene transcription. For example, for telomerase, transcriptional activators of gene expression include c-myc, NFκB, or the estrogen receptor, and inhibitors of telomerase gene transcription include Mad and p53.

As will be apparent to one of ordinary skill in the art, certain genes may function in multiple capacities to alter the phenotype of cells. For example, the ectopic expression of IL-6 will promote growth, but may also inhibit apoptosis by increasing the activity or expression of polypeptides that inhibit apoptosis. As mentioned above, p53 is an inhibitor of telomerase expression, but also is a tumor suppressor. Therefore, inhibition of p53 activity, such as by the ectopic expression of a p53 dominant negative mutant, will inhibit apoptosis through reduced inhibition of telomerase expression, and will also inhibit tumor suppressor activity directly by interfering with p53. Other combinations of ectopically expressed genes may have other mutually beneficial effects on the phenotype of the fusion partner cell or hybrids produced therefrom.

The cell line in which genes are ectopically expressed may have single or multiple copies of the ectopic gene per cell. Increasing the number of copies of the ectopic gene in the fusion partner cell may improve the efficiency with which hybrid cells acquire a copy of the ectopic gene.

Cells that have acquired an ectopic gene can be identified by single cell cloning and analysis of the cloned cells for the presence of ectopically expressed mRNA or protein (using RT-PCR with primers specific for the ectopic mRNA), or for the altered genomic DNA sequences that ectopically express the gene (e.g., using PCR with primers specific for the altered DNA sequences). Cloned cells can also be analyzed for the presence of the products of ectopically expressed polypeptides using Western blotting, FACS, and the like. Moreover, cells can be analyzed for other phenotypic effects caused by activation or inhibition of cellular pathways by the ectopic expression of genes.

In many instances, immortal mammalian cell lines of the present invention express or are modified to express at least one (one or more) gene that encodes a selectable marker, which make it easier to identify cells that express an ectopic gene. The selectable marker encoded by the gene can be one that confers resistance to a drug, such as resistance to G418, hygromycin, puromycin, bleomycin or another drug. Alternatively, the immortal mammalian cell lines of the present invention can express at least one gene that encodes a chromogenic protein, such as Green Fluorescent Protein, Blue Fluorescent Protein, Red Fluorescent Protein, Yellow Fluorescent Protein or beta-galactosidase. In one embodiment, the identification of immortal mammalian cells that have acquired an ectopic gene(s) is facilitated by culturing cells with an antibiotic such as puromycin; cells that have not acquired the ectopic gene(s) do not survive in the presence of the antibiotic.

Any B-lineage cell line, in particular immortal mammalian cell lines and those of murine and human origin, is suitable as a fusion partner cell line within the scope of the present invention, provided it has undergone manipulation that would ensure the expression of an ectopic gene(s) in hybrid cells formed with the cell line. This includes immortal cell lines of B-cell lineage regardless of whether they also express the ectopically expressed gene(s) from an endogenous gene. Such B-lineage cell lines, modified to express an ectopic gene, are a subject of this invention.

Myeloma cell lines are immortal, malignant B-lineage cell lines. Myeloma cell lines that express an two or more ectopic genes that alter cell phenotype, or that express genes that inhibit tumor suppressor activity (optionally in combination with other genes) have not been used previously as fusion partners for the formation of hybrid cells that secrete human antibodies. Thus myeloma cell lines that express ectopic genes and their use in the formation of hybrid cells that express ectopic genes are specific embodiments of the present invention.

Lymphoblastoid cell lines are immortal human B-lineage cell lines that have been infected in vivo or in vitro with the Epstein-Barr Virus and have been established in cell culture. As defined herein, lymphoblastoid cell lines also comprise B-lineage cells that express Epstein-Barr Virus antigens. Lymphoblastoid cell lines that express two or more ectopic genes that alter cell phenotype, or that express genes that inhibit tumor suppressor activity (optionally in combination with other genes), have not been used previously as fusion partners for the formation of hybrid cells that secrete human antibodies. Lymphoblastoid cell lines that express ectopic genes and their use in the formation of hybrid cells that express ectopic genes are specific embodiments of the present invention.

The SP2/0 cell line is an immortal murine myeloma cell line (a malignant B-lineage cell) that expresses an endogenous murine telomerase gene and is a frequently used as a fusion partner for forming murine hybridomas (M. Shulman et al, *Nature* 276:269 (1978)). As described herein, it was modified so that it expresses genes ectopically. The resulting cell lines are specific embodiments of the present invention. As described below, ectopic expression of the genes results in improved ability of this cell line to function as a fusion partner in fusions with human and murine B-cells (compared with the ability of the SP2/0 cell line).

A further embodiment of fusion partners of the present invention is primary B-lineage cells that ectopically express genes in such a manner that expression is not subject to repression in hybrid cells formed by fusion of such primary B-cell lineage cells with an appropriate fusion cell. For example, primary B-lineage cells that have not been adapted to continuous growth in vitro express telomerase from their endogenous telomerase genes in a transient fashion when they are stimulated with growth factors or other mitogens (N. P. Weng et al, *Immunity* 9:151 (1998)). This transient telomerase expression is not associated with unlimited replicative potential, perhaps because telomerase expression is transient or because other genetic and epigenetic events required for sustained in vitro growth have not occurred. However, introduction of a constitutively expressed ectopic telomerase gene has contributed to the immortalization of primary T-lineage cells, and would therefore likely contribute to the immortalization of primary B-lineage cells. The ectopic telomerase gene, resistant to repression in hybrid cells, would facilitate the formation of fused cells that express an ectopic telomerase gene. Therefore, primary B-lineage cells that have been engineered to ectopically express a telomerase gene in a manner that is not subject to repression in hybrid cells, and also ectopically express at least one other gene, are a specific embodiment of fusion partners of the present invention. Primary B-lineage cells that ectopically express other genes, or that express combinations of ectopically expressed genes, also are embodiments of the invention.

Fusion partner cells that have undergone genetic or other modifications that improve their effectiveness as fusion partners are also specific embodiments of the present invention. Such modifications could, for instance, improve the rate at which cell fusions form viable hybrids, improve the growth properties of the hybrids, provide or induce the formation of selectable marker genes for the identification of successful hybrids, and improve other properties of the hybrids such as the level of immunoglobulin expression.

Fusion partner cell lines derived from organisms other than humans and old-world primates may lead to the creation of hybrid cells that secrete antibodies modified by Galα1-3Gal glycosylation. Humans and old-world primates have native, high-titer antibodies that recognize this antigen that may compromise the ability of antibodies bearing this antigen to be used as medical therapeutics. For instance, immune complexes may form that could lead to premature clearing of antibodies bearing this antigen from the serum. Therefore, immortal mammalian cell lines that are modified so as to be deficient in the enzyme α-1,3-galactosyltransferase are specific embodiments of the present invention.

The hybrid cells that result from fusion of the fusion partner cell lines and fusion cells described herein are specific embodiments of the present invention, as are the antibodies produced by the hybrid cells.

Also within the scope of the invention are kits comprising the fusion partner cells of the invention, or hybrid cells prepared therefrom and instructions for use. The kits can further contain at least one additional reagent, such as a fusion reagent, or one or more additional genes for ectopic expression (e.g., in a viral vector). The kits can be used to prepare hybrid cells from a fusion cell of choice.

6. Antibodies and Uses Therof

The cells and methods of the invention described herein provide improved production of hybrid cells, including antibody-expressing cells. In addition to improved cloning of such cells and improved production of antibodies, the invention permits, for the first time, screening of the antibody repertoire of humans already exposed to antigens for antibodies that specifically react with medically interesting antigens. Prior to the invention, the low frequencies of hybridoma techniques using human cells prevented any investigation of human antibodies selected by the human immune system in humans. In particular, humans exposed to disease, such as infectious disease or cancer, in which antibody responses play a role in recovery from the disease, have immune memory of antibodies effective against the diseases. These antibodies now can be isolated and utilized for therapeutic and diagnostic purposes.

As used herein, the term "antibody" refers to a glycoprotein comprising at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDRs), interspersed with regions that are more conserved, termed framework regions (FRs). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody as used herein, refers to one or more portions of an antibody that retain the ability to specifically bind to an antigen. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546) which consists of a $V_H$ domain; and (vi) an isolated complementarity determining region (CDR). Furthermore, although the two domains of the Fv fragment, V and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference, as well as by other techniques known to those with skill in the art. The fragments are screened for utility in the same manner as are intact antibodies.

An "isolated antibody", as used herein, is intended to refer to an antibody which is substantially free of other antibodies having different antigenic specificities (e.g., an isolated antibody that specifically binds to a particular cancer antigen is substantially free of antibodies that specifically bind antigens other than that particular cancer antigen). An isolated antibody that specifically binds to an epitope, isoform or variant of an antigen may, however, have cross-reactivity to other related antigens, e.g., from other species. Moreover, an isolated antibody may be substantially free of other cellular material and/or chemicals. As used herein, "specific binding" refers to antibody binding to a predetermined antigen. Typically, the antibody binds with an affinity that is at least two-fold greater than its affinity for binding to a non-specific antigen (e.g., BSA, casein) other than the predetermined antigen or a closely-related antigen.

The isolated antibodies of the invention encompass various antibody isotypes, such as IgG1, IgG2, IgG3, IgG4, IgM, IgA1, IgA2, IgAsec, IgD, IgE. As used herein, "isotype" refers to the antibody class (e.g. IgM or IgG1) that is encoded by heavy chain constant region genes. The antibodies can be full length or can include only an antigen-binding fragment such as the antibody constant and/or variable domain of IgG1, IgG2, IgG3, IgG4, IgM, IgA1, IgA2, IgAsec, IgD or IgE or could consist of a Fab fragment, a F(ab')$_2$ fragment, or a Fv fragment.

In preferred embodiment, human somatic cells capable of producing antibody, specifically B lymphocytes, are suitable for fusion with the fusion partner cells of the invention. While B lymphocytes from biopsied spleens, tonsils or lymph nodes of an individual may be used, the more easily accessible peripheral blood B lymphocytes are preferred. The lymphocytes may be derived from patients with diagnosed diseases (e.g., cancer, infectious disease, autoimmune disease), preferably after those patients recover from the disease, or from subjects without clinically-identifiable disease.

In other embodiments, the antibodies can be recombinant antibodies. The term "recombinant antibody," as used herein, is intended to include antibodies that are prepared, expressed, created or isolated by recombinant means, such as antibodies isolated from an animal (e.g., a mouse) that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

The methods of the invention provide for enhanced fusion and cloning of hybridomas from the B cells of any species. This includes B cells of animals (e.g., mouse) injected by an antigen of a different species (e.g., human) in order to make antibodies against the human antigen. Accordingly, the invention includes those antibodies made by hybridomas produced from the fusion of conventionally generated antibody-producing cells and the fusion partner cells of the invention. In one particular embodiment of the invention, B cells from mice having grafted human immunoglobulin genes (e.g., those of Abgenix or Medarex) can be fused to fusion partner cells according to the invention, to increase the fusion frequency, hybrid formation, hybrid cell cloning, antibody secretion, and the like of the B cells.

In yet other embodiments, the antibodies can be chimeric or humanized antibodies. As used herein, the term "chimeric antibody" refers to an antibody, that combines the murine variable or hypervariable regions with the human constant region or constant and variable framework regions. As used herein, the term "humanized antibody" refers to an antibody that retains only the antigen-binding CDRs from the parent antibody in association with human framework regions (see, Waldmann, 1991, *Science* 252:1657). Such chimeric or humanized antibodies retaining binding specificity of the murine antibody are expected to have reduced immunogenicity when administered in vivo for diagnostic, prophylactic or therapeutic applications according to the invention. The methods of the invention can enhance the antibody producing capacity of cells that secrete these types of antibodies.

In preferred embodiments, the antibodies are human antibodies. The term "human antibody," as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse have been grafted onto human framework sequences (referred to herein as "humanized antibodies").

According to an alternative embodiment, the monoclonal antibodies of the present invention can be modified to be in the form of a bispecific antibody, or a multispecific antibody. The term "bispecific antibody" is intended to include any agent, e.g., a protein, peptide, or protein or peptide complex, which has two different binding specificities which bind to, or interact with (a) a cell surface antigen and (b) an Fc receptor on the surface of an effector cell. The term "multispecific antibody" is intended to include any agent, e.g., a protein, peptide, or protein or peptide complex, which has more than two different binding specificities which bind to, or interact with (a) a cell surface antigen, (b) an Fc receptor on the surface of an effector cell, and (c) at least one other component. Accordingly, the invention includes, but is not limited to, bispecific, trispecific, tetraspecific, and other multispecific antibodies which are directed preferably to cell surface antigens, and to Fc receptors on effector cells. The term "bispecific antibodies" further includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites (see e.g., Holliger, P., et al. (1993) *Proc. Natl. Acad. Sci. USA* 90:6444-6448; Poijak, R. J., et al. (1994) *Structure* 2:1121-1123).

For example, a bispecific antibody can be formed of an antigen-binding region specific for a tumor antigen and an antigen-binding region specific for an effector cell which has tumoricidal or tumor inhibitory activity. The two antigen-binding regions of the bispecific antibody are either chemically linked or can be expressed by a cell genetically engineered to produce the bispecific antibody. (See generally, Fanger et al., 1995 *Drug News & Perspec.* 8(3):133-137). Suitable effector cells having tumoricidal activity include but are not limited to cytotoxic T-cells (primarily $CD8^+$ cells), natural killer cells, etc. An effective amount of a bispecific antibody according to the invention is administered to a cancer patient and the bispecific antibody kills and/or inhibits proliferation of the malignant cells after localization at sites of primary or metastatic tumors bearing the antigen.

An antibody can be linked to a detectable marker, an antitumor agent or an immunomodulator. Antitumor agents can include cytotoxic agents and agents that act on tumor neovasculature. Detectable markers include, for example, radioactive or fluorescent markers. Cytotoxic agents include cytotoxic radionuclides, chemical toxins and protein toxins.

The cytotoxic radionuclide or radiotherapeutic isotope preferably is an alpha-emitting isotope such as $^{225}Ac$, $^{211}At$, $^{212}Bi$, or $^{213}Bi$. Alternatively, the cytotoxic radionuclide may a beta-emitting isotope such as $^{186}Rh$, $^{188}Rh$, $^{177}Lu$, $^{90}Y$, $^{131}I$ or $^{67}Cu$. Further, the cytotoxic radionuclide may emit Auger and low energy electrons and include the isotopes $^{125}I$, $^{123}I$ or $^{77}Br$.

Suitable chemical toxins or chemotherapeutic agents include members of the enediyne family of molecules, such as calicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouracil. Toxins that are less preferred in the compositions and methods of the invention include poisonous lectins, plant toxins such as ricin, abrin, modeccin, botulina and diphtheria toxins. Of course, combinations of the various toxins could also be coupled to one antibody molecule thereby accommodating variable cytotoxicity. Other chemotherapeutic agents are known to those skilled in the art.

Agents that act on the tumor vasculature can include tubulin-binding agents such as combrestatin A4 (Griggs et al., *Lancet Oncol.* 2:82, 2001), angiostatin and endostatin (reviewed in Rosen, *Oncologist* 5:20, 2000, incorporated by reference herein), interferon inducible protein 10 (U.S. Pat. No. 5,994,292), and the like. Immunomodulators suitable for conjugation to antibodies include α-interferon, γ-interferon, and tumor necrosis factor alpha (TNFα).

The coupling of one or more toxin molecules to the antibodies of the invention is envisioned to include many chemical mechanisms, for instance covalent binding, affinity binding, intercalation, coordinate binding, and complexation. The toxic compounds used to prepare the immunotoxins are attached to the antibodies or binding fragments thereof by standard protocols known in the art.

The covalent binding can be achieved either by direct condensation of existing side chains or by the incorporation of external bridging molecules. Many bivalent or polyvalent agents are useful in coupling protein molecules to other proteins, peptides or amine functions, etc. For example, the literature is replete with coupling agents such as carbodiimides, diisocyanates, glutaraldehyde, diazobenzenes, and hexamethylene diamines. This list is not intended to be exhaustive of the various coupling agents known in the art but, rather, is exemplary of the more common coupling agents.

In preferred embodiments, it is contemplated that one may wish to first derivative the antibody, and then attach the toxin component to the derivatized product. Suitable cross-linking agents for use in this manner include, for example, SPDP (N-succinimidyl-3-(2-pyridyldithio)propionate), and SMPT, 4-succinimidyl-oxycarbonyl-methyl-(2-pyridyldithio)toluene.

In addition, protein toxins can be fused to the antibody or binding fragment by genetic methods to form a hybrid immunotoxin fusion protein. To make a fusion immunotoxin protein in accordance with the invention, a nucleic acid molecule is generated that encodes an antibody, a fragment of an antibody, a single chain antibody, or a subunit of an antibody linked to a protein toxin. Such fusion proteins contain at least a targeting agent (e.g., antibody subunit) and a toxin, operatively attached. The fusion proteins may also include additional peptide sequences, such as peptide spacers which operatively attach the targeting agent and toxin compound, as long as such additional sequences do not appreciably affect the targeting or toxin activities of the fusion protein. The two proteins can be attached by a peptide linker or spacer, such as a glycine-serine spacer peptide, or a peptide hinge, as is well known in the art. Thus, for example, the C-terminus of an antibody or fragment thereof can be fused to the N-terminus of the protein toxin molecule to form an immunotoxin that retains the binding properties of the antibody. Other fusion arrangements will be known to one of ordinary skill in the art.

To express the fusion immunotoxin, the nucleic acid encoding the fusion protein is inserted into an expression vector in accordance with standard methods, for stable expression of the fusion protein, preferably in mammalian cells, such as CHO cells. The fusion protein can be isolated and purified from the cells or culture supernatant using standard methodology, such as an antigen affinity column.

Radionuclides typically are coupled to an antibody by chelation. For example, in the case of metallic radionuclides, a bifunctional chelator is commonly used to link the isotope to the antibody or other protein of interest. Typically, the chelator is first attached to the antibody, and the chelator-antibody conjugate is contacted with the metallic radioisotope. A number of bifunctional chelators have been developed for this purpose, including the diethylenetriamine pentaacetic acid (DTPA) series of amino acids described in U.S. Pat. Nos. 5,124,471, 5,286,850 and 5,434,287, which are incorporated herein by reference. As another example, hydroxamic acid-based bifunctional chelating agents are described in U.S. Pat. No. 5,756,825, the contents of which are incorporated herein. Another example is the chelating agent termed p-SCN-Bz-HEHA (1,4,7,10,13,16-hexaazacyclo-octadecane-N,N',N'', N''',N'''',N'''''-hexaacetic acid) (Deal et al., *J. Med. Chem.* 42:2988, 1999), which is an effective chelator of radiometals such as $^{225}Ac$.

In another aspect, the invention provides compositions comprising an isolated antibody, an antibody derivatized or linked to other functional moieties, or an antigen-binding fragment thereof or a combination of one or more of the aforementioned antibodies or antigen-binding fragments thereof. The compositions include a physiologically or pharmaceutically acceptable carrier, excipient, or stabilizer mixed with the isolated antibody or antigen-binding fragment thereof. In a preferred embodiment, the compositions include a combination of multiple (e.g., two or more) isolated antibodies or antigen-binding portions thereof of the invention. Preferably, each of the antibodies or antigen-binding portions thereof of the composition binds to a distinct epitope or antigen. In one embodiment, antibodies having complementary activities are used in combination, e.g., as a pharmaceutical composition, comprising two or more antibodies. For example, an antibody that mediates highly effective cytolysis of target cells in the presence of effector cells can be combined with another antibody that inhibits the growth of cells expressing an antigen. As used herein, "target cell" shall mean any undesirable cell in a subject (e.g., a human or animal) that can be targeted by a composition of the invention.

Pharmaceutical compositions of the invention also can be administered in combination therapy, i.e., combined with other agents. For example, the combination therapy can include a composition of the present invention with at least one anti-tumor agent, immunomodulator, immunostimulatory agent, or other conventional therapy. As used herein, "pharmaceutically acceptable carrier" or "physiologically acceptable carrier" includes any and all salts, solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody may be coated in a material to protect the compound from the action of acids and other natural conditions that may inactivate the compound.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents, such as supplementary immune potentiating agents including adjuvants and cytokines. When used in medicine, the salts should be pharmaceutically acceptable, but non-pharmaceutically acceptable salts may conveniently be used to prepare pharmaceutically-acceptable salts thereof and are not excluded from the scope of the invention.

A salt retains the desired biological activity of the parent compound and does not impart any undesired toxicological effects (see e.g., Berge, S. M., et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chioroprocaine, choline, diethanolamine, ethylenediamine, procaine and the like.

An antibody composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for parenteral administration conveniently comprise a sterile aqueous or non-aqueous preparation of antibodies, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulations suitable for oral, subcutaneous, intravenous, intramuscular, etc. administration can be found in *Remington's Pharmaceutical Sciences*, Mack Publishing Co., Easton, Pa.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

The therapeutics of the invention can be administered by any conventional route, including injection or by gradual infusion over time. The administration may, for example, be oral, intravenous, intraperitoneal, intramuscular, intracavity, intratumor, or transdermal. When antibodies are used therapeutically, preferred routes of administration include intravenous and by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences,*

18th edition, 1990, pp. 1694-1712; incorporated by reference). Those of skill in the art can readily determine the various parameters and conditions for producing antibody aerosols without resorting to undue experimentation.

The compositions of the invention are administered in effective amounts. An "effective amount" is that amount of an antibody composition that alone, or together with further doses, produces the desired response, e.g. treats a malignancy or infectious disease in a subject. This may involve only slowing the progression of the disease temporarily, although more preferably, it involves halting the progression of the disease permanently. This can be monitored by routine methods. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of antibodies for producing the desired response in a unit of weight or volume suitable for administration to a patient. The response can, for example, be measured by determining the physiological effects of the antibody composition, such as regression of a tumor or decrease of disease symptoms. Other assays will be known to one of ordinary skill in the art and can be employed for measuring the level of the response.

The doses of antibodies administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, doses can range from about 10 μg/kg to about 100,000 μg/kg. Based upon the composition, the dose can be delivered continuously, such as by continuous pump, or at periodic intervals. Desired time intervals of multiple doses of a particular composition can be determined without undue experimentation by one skilled in the art. Other protocols for the administration of antibody compositions will be known to one of ordinary skill in the art, in which the dose amount, schedule of administration, sites of administration, mode of administration and the like vary from the foregoing.

In general, doses of radionuclide delivered by the antibodies of the invention can range from about 0.01 mCi/Kg to about 10 mCi/kg. Preferably the dose of radionuclide ranges from about 0.1 mCi/Kg to about 1.0 mCi/kg. The optimal dose of a given isotope can be determined empirically by simple routine titration experiments well known to one of ordinary skill in the art.

Administration of antibody compositions to mammals other than humans, e.g. for testing purposes or veterinary therapeutic purposes, is carried out under substantially the same conditions as described above.

The antibody compositions of the present invention have in vitro and in vivo diagnostic and therapeutic utilities. For example, these molecules can be administered to cells in culture, e.g. in vitro or ex vivo, or in a subject, e.g., in vivo, to treat, prevent or diagnose a variety of disorders. As used herein, the term "subject" is intended to include humans and non-human animals. Preferred subjects include a human patient having a disorder characterized by expression, typically aberrant expression (e.g., overexpression) of an antigen.

One aspect of the present invention relates to a method of detecting cancerous cells or portions thereof in a biological sample (e.g., histological or cytological specimens, biopsies and the like), and, in particular, to distinguish malignant tumors from normal tissues and non-malignant tumors. This method involves providing an antibody or an antigen-binding binding fragment thereof, probe, or ligand, which binds to a cancer antigen. The antibody is bound to a label that permits the detection of the cells or portions thereof upon binding of the antibody to the cells or portions thereof. The biological sample is contacted with the labeled antibody under conditions effective to permit binding of the antibody to the antigen of any of the cells or portions thereof in the biological sample. The presence of cells expressing the antigen or portions thereof in the biological sample is detected by detection of the label. In one preferred form, the contact between the antibody and the biological sample is carried out in a living mammal and involves administering the antibody to the mammal under conditions that permit binding of the antibody to the antigen expressed by any of the cells or portions thereof in the biological sample. Again, such administration can be carried out by any suitable method known to one of ordinary skill in the art.

In addition, the antibodies of the present invention can be used in immunofluorescence techniques to examine tissue, cell and bodily fluid specimens. In a typical protocol, slides containing cryostat sections of frozen, unfixed tissue biopsy samples or cytological smears are air dried, formalin or acetone fixed, and incubated with the antibody preparation in a humidified chamber at room temperature. The slides are then washed and further incubated with a preparation of a secondary antibody directed against the antibody, for example an anti-human immunoglobulin if the monoclonal antibodies used are derived from the fusion of a human lymphocyte and a human fusion partner cell line. This secondary antibody is tagged with a compound, for instance rhodamine or fluorescein isothiocyanate, that fluoresces at a particular wavelength. The staining pattern and intensities within the sample are then determined by fluorescent light microscopy and optionally photographically recorded.

As yet another alternative, computer enhanced fluorescence image analysis or flow cytometry can be used to examine tissue specimens or exfoliated cells, i.e., single cell preparations from aspiration biopsies of tumors using the antibodies of the invention. The antibodies of the invention are therefore useful in quantitation of live tumor cells, i.e., single cell preparations from aspiration biopsies of tumors by computer enhanced fluorescence image analyzer or with a flow cytometer. The antibodies of the invention are particularly useful in such assays to differentiate benign from malignant tumors when the antigen to which the antibodies bind is expressed in increased amounts by malignant tumors as compared to benign tumors or normal cells. The percent antigen positive cell population, alone or in conjunction with determination of other attributes of the cells (e.g., DNA ploidy of these cells), may, additionally, provide very useful prognostic information by providing an early indicator of disease progression.

In yet another alternative embodiment, the antibodies of the present invention can be used in combination with other known antibodies to provide additional information regarding the malignant phenotype of a cancer.

The method of the present invention can be used to screen patients for diseases associated with the presence of cancerous cells or portions thereof. Alternatively, it can be used to identify the recurrence of such diseases, particularly when the disease is localized in a particular biological material of the patient. For example, recurrence of prostatic disease in the prostatic fossa may be encountered following radical prostatectomy. Using the method of the present invention, this recurrence can be detected by administering a short range radiolabeled antibody to the mammal and then detecting the label rectally, such as with a transrectal detector probe.

The antibodies or antigen-binding fragments thereof can also be utilized in in vivo therapy of cancer. The antibodies can be used alone or covalently attached, either directly or via linker, to a compound which kills and/or inhibits proliferation of the malignant cells or tissues following administration and localization of the conjugates. When the antibody is used by itself, it may mediate tumor destruction by complement fixation or antibody-dependent cellular cytotoxicity. Alternatively, the antibody may be administered in combination with a chemotherapeutic drug to result in synergistic therapeutic effects (Baslya and Mendelsohn, 1994 *Breast Cancer Res. and Treatment* 29:127-138). A variety of different types of substances can be directly conjugated to the antibody for therapeutic uses, including radioactive metal and non-metal isotopes, chemotherapeutic drugs, toxins, etc. as described above and known in the art (see, e.g., Vitetta and Uhr, 1985, *Annu. Rev. Immunol.* 3:197).

The antibodies or antigen-binding fragments thereof of the invention can also be administered together with complement. Accordingly, within the scope of the invention are compositions comprising antibodies or antigen-binding fragments thereof and serum or complement. These compositions are advantageous in that the complement is located in close proximity to the human antibodies or antigen-binding fragments thereof. Alternatively, the antibodies or antigen-binding fragments thereof of the invention and the complement or serum can be administered separately.

The antibodies can be administered with one or more immunostimulatory agents to induce or enhance an immune response, such as IL-2 and immunostimulatory oligonucleotides (e.g., those containing CpG motifs). Preferred immunostimulatory agents stimulate specific arms of the immune system, such as natural killer (NK) cells that mediate antibody-dependent cell cytotoxicity (ADCC).

The antibodies or antigen-binding fragments thereof of the present invention can be used in conjunction with other therapeutic treatment modalities. Such other treatments include surgery, radiation, cryosurgery, thermotherapy, hormone treatment, chemotherapy, vaccines, antibiotic therapies, antiviral therapies and other immunotherapies.

Also encompassed by the present invention is a method which involves using the antibodies or antigen-binding fragments thereof for prophylaxis. For example, these materials can be used to prevent or delay development or progression of cancer.

Also within the scope of the invention are kits comprising the antibody compositions of the invention and instructions for use. The kits can further contain at least one additional reagent, such as complement, or one or more additional antibodies of the invention (e.g., an antibody having a complementary activity which binds to an antigen distinct from the first antibody).

Kits containing the antibodies or antigen-binding fragments thereof of the invention can be prepared for in vitro diagnosis, prognosis and/or monitoring of disease by the immunohistological, immunocytological and immunoserological methods described above. The components of the kits can be packaged either in aqueous medium or in lyophilized form. When the antibodies or antigen-binding fragments thereof are used in the kits in the form of conjugates in which a label moiety is attached, such as an enzyme or a radioactive metal ion, the components of such conjugates can be supplied either in fully conjugated form, in the form of intermediates or as separate moieties to be conjugated by the user or the kit.

A kit may comprise a carrier being compartmentalized to receive in close confinement therein one or more container means or series of container means such as test tubes, vials, flasks, bottles, syringes, or the like. A first of said container means or series of container means may contain one or more antibodies or antigen-binding fragments thereof. A second container means or series of container means may contain a label or linker-label intermediate capable of binding to the primary antibodies (or fragment thereof).

Kits for use in in vivo tumor localization and therapy method containing the antibodies or antigen-binding fragments thereof conjugated to other compounds or substances can be prepared. The components of the kits can be packaged either in aqueous medium or in lyophilized form. When the antibodies or antigen-binding fragments thereof are used in the kits in the form of conjugates in which a label or a therapeutic moiety is attached, such as a radioactive metal ion or a therapeutic drug moiety, the components of such conjugates can be supplied either in fully conjugated form, in the form of intermediates or as separate moieties to be conjugated by the user of the kit.

The present invention is illustrated by the following examples, which are not intended to be limiting in any way.

EXAMPLES

Methods and Materials

Cell Culture and Cell Fusions

The SP2/0 cell line and the SP2/0 mIL-6 cell line (ATCC, Manassas, Va.) were maintained in RPMI with 10% heat-inactivated fetal calf serum, with penicillin/streptomycin. The SKO-007 J3 cell line (ATCC) was maintained in RPMI with 15-20% heat-inactivated fetal calf serum, with penicillin/streptomycin. 293T cells (ATCC) were maintained in DME with 10% heat-inactivated fetal calf serum, with penicillin/streptomycin. Antibiotic selection was in the presence of 0.5 micrograms/ml puromycin, or 500 µg/ml G418. Fusions were performed with polyethylene glycol (Sigma, St. Louis, Mo.) and selection in HAT medium (GIBCO-BRL, Rockville, Md.) following standard techniques (E. Harlow et al, *Antibodies: A Laboaratory Manual* Cold Spring Harbor Laboratory, Cold Spring Harbor, 1988). Fusions with murine and human fusion partner cell lines used 50% and 37% polyethylene glycol, respectively.

Retroviral Infection

A retroviral transfer vector containing an hTERT cDNA in combination with a puromycin selectable marker gene (MSCV Puro hTERT) was constructed using standard recombinant DNA techniques. Retrovirus-containing supernatants were produced in 293T cells using the following variation on standard techniques: 500,000 cells were plated on 6-cm dishes in 4-ml culture medium. The following day, 1 microgram retroviral vector DNA (MSCV Puro hTERT) and 1 microgram of packaging plasmid (pCL Eco (R. K. Naviaux et al, *J. Virol.* 70:5701 1996)) were co-transfected using FuGENE (Roche Applied Science, Indianapolis, Ind.) using standard protocols. The next day, the medium was replaced with 4 ml RPMI medium. Recipient cells (SP2/0) were seeded in 12-well dishes: 500,000 cells in 2 ml medium. The following day, the supernatant from the transfected 293T cells (containing infectious, replication incompetent retroviruses) was filtered through a 45 micron syringe filter, supplemented with 8 micrograms/ml polybrene, and applied to the recipient cells. Cells were spun in a tabletop centrifuge for 90 minutes at 1500 RPM at 32° C. Cells were then moved to 37° C. for an additional 90 minutes. The retroviral supernatant was then replaced with fresh culture medium. The spin/infection process was repeated 24 hours later. The day after the second infection, the cells were brought up to 5 ml total volume with fresh medium containing puromycin (Sigma-Aldrich, St. Louis, Mo.) selection. This general protocol was also used for the retroviral infection of the J3 cell lines, except that the pCL AMPHO (R. K. Naviaux et al, *J. Virol.* 70:5701 1996)) packaging plasmid was used and the cells and viruses were handled under BL2+-level containment protocols. Following establishment that the infected J3 cells did not produce any replication-competent retrovirus using a standard lateral transfer assay, the cells were moved to the BL2-level containment facility.

Cells that had been infected with the GFP-expressing retroviruses were sorted on a FACS-Star flow cytometry machine (Becton-Dickinson, Franklin Lakes, N.J.). J3 cell lines were sorted as polyclonal populations. SP2/0 cell lines were sorted as individual cells into wells of a 96-well plate. Individual clones were grown out and characterized, including the SP2/0 MPT hIL-6 clones C9, F11 and F12.

Other recombinant, replication-defective retroviruses have been produced with the following retroviral transfer vectors: pBN DD, encoding a truncated p53 protein and a neomycin (G418) selectable marker gene; pMIG hIL-6, encoding a human IL-6 cDNA (see below) and a GFP gene that lies downstream of an internal ribosome entry site (IRES); pGD v-abl, encoding a v-abl gene and a G418 selectable marker gene, courtesy of George Q. Daley (Whitehead Institute, Cambridge, Mass.).

Human Peripheral Blood Mononuclear Cells (PBMCs) and Human Splenocytes.

Human PBMCs and human splenocytes were obtained as anonymous discarded samples under a protocol approved by the Institutional Review Board of the Human Research Committee of the Massachusetts General Hospital, protocol #2000-P-001589/2. All human samples were handled following the guidelines of Universal Precautions under the direction of the Biosafety Committee of the Whitehead Institute for Biomedical Research. Human PBMCs were obtained by leukopheresis or phlebotomy and purified over a Ficoll-Paque PLUS gradient (Amersham Pharmacia Biotech, Uppsala, Sweden) following standard protocols. Human spleen samples, obtained at surgery, were cut into pieces with a #11 scalpel, placed in RPMI 10% heat-inactivated fetal calf serum, smashed with the plunger end of a 20 ml syringe, and then filtered through a 70 micron Cell Strainer (Becton Dickinson, Franklin Lakes, N.J.) prior to purification over a Ficoll Paque PLUS gradient. For storage cells were frozen in 40% RPM 10% DMSO, 50% heat inactivated fetal calf serum. The cells were stimulated prior to fusion with pokeweed mitogen using standard techniques.

RT-PCR.

Five micrograms of total RNA was used in a cDNA synthesis reaction using the First-strand cDNA synthesis kit (Amersham Pharmacia, Piscataway, N.J.), with the reverse hTERT and GAPDH primers, each at 2 mM. PCR reactions were run in standard conditions with 2.5 units Taq Polymerase (Perkin Elmer Life Sciences, Boston, Mass.) complexed with Taq Start antibody (Clontech Laboratories, Inc., Palo Alto, Calif.), and $^{32}$P-labeled forward primers. Reactions analyzing each mRNA were run separately. Five microliters of cDNA were used in the hTERT and mTERT reactions; one microliter of a 1:400 dilution of the cDNA was used in the GAPDH reactions. PCR reactions were cycled 25 times: 94° C. for 30 s, 60° C. for 30 s, 72° C. for 30 s. Ten microliters of each reaction were analyzed with 8% PAGE, 1× TBE. mTERT primers: AN1 forward (TGAGCGGA-CAAAACATCC; SEQ ID NO:1) AC1 reverse (AG-GCTCGTCTTAATTGAGGT; SEQ ID NO:2) hTERT primers: LT5 forward (CGG AAG AGT GTC TGG AGC AA; SEQ ID NO:3) and LT6 reverse (LT6 GGA TGA AGC GGA GTC TGG A; SEQ ID NO:4) (20) GAPDH primers: GAPDH1 forward (GAC CCC TTC ATT GAC CTC AAC: SEQ ID NO:5) and GAPDH2 reverse primer (CTT CTC CAT GGT GGT GAA GA;SEQ ID NO:6).

Figure 3:
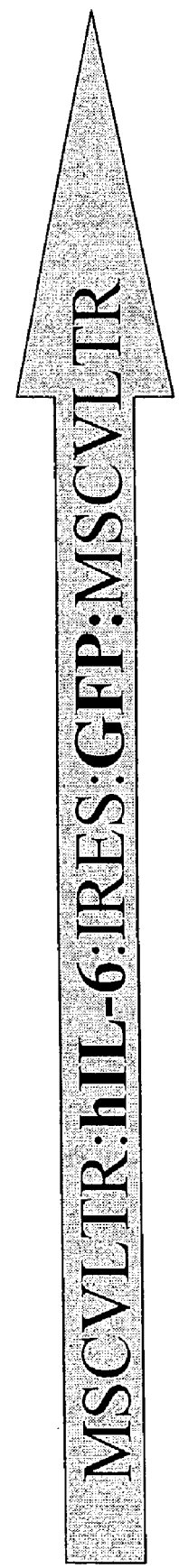
FIG. 3 is a diagram of a retroviral gene plasmid that encodes human IL-6 and GFP from a bi-cistronic mRNA. The schematic drawing illustrates the relevant domains of the plasmid, pMSCV IRES GFP hIL-6. MSCV LTR, the LTR of the murine stem cell virus. hIL-6, the human IL-6 gene. IRES, an internal ribosome entry site. GFP, the green fluorescent protein gene.

The human IL-6 cDNA was obtained by reverse-transcriptase PCR of RNA obtained from the T24 bladder carcinoma cell line (ATCC), using the primers: hIL-6 5' CGG-GATCCGAAGCCACCATGAACTCCTTCTCCACAAGC (SEQ ID NO:7) and hIL-6 3' CGGAATTCGTCGAGAAC-TACATTTGCCGAAGAGCCC (SEQ ID NO: 8). The first-strand synthesis was performed as described above. The PCR reactions were cycled in a touchdown protocol: first 10 cycles: 94° C. for 30 s, 65° C. decreasing by 1 degree each cycle for 30 s, 72° C. for 30 s; next 15 cycles: 94° C. for 30 s, 55° C. for 30 s, 72° C. for 30 s. PCR products were purified on an agarose gel and cloned using a TOPO-TA Cloning Kit (Invitrogen, Carlsbad, Calif.). The sequence of the hIL-6 cDNA was verified (Research Genetics, Huntsville, Ala.), and the cloned cDNA was subcloned into the BglII and EcoRI sites of the retroviral vector, pMSCV-IRES GFP, (pMIG, courtesy of Luk van Parijs, MIT, Cambridge, Mass.) (FIG. 3).

ELISA Assays.

Human immunoglobulin secretion was analyzed using standard techniques for ELISA assays (E. Harlow et al, *Antibodies: A Laboratory Manual* (Cold Spring Harbor Laboratory, Cold Spring Harbor, 1988). Wells in standard 96-well ELISA plates were coated with thirty microliters of primary 01 Rabbit anti-human IgG specific for heavy and light chains antibodies from (Southern Biotechnology Associates, Inc., Birmingham, Ala.) at a concentration of 2 micrograms/ml. The same antibody, conjugated to horseradish peroxidase, was used as a secondary (Southern Biotechnology Associates, Inc.) at a 1:3000 dilution in phosphate buffered saline/ 0.1% bovine serum albumin. Assays were developed using standard techniques with a chromogenic substrate.

Human IL-6 expression in the J3 cell lines and the SP2/0 cell lines was confirmed using the Pelikine Compact human IL-6 ELISA kit (Research Diagnostics, Flanders, N.J.).

Gene Sequences

The genes expressed, their Genbank accession numbers, and origins are as follows: hTERT, AF018167 (courtesy of the laboratory of Robert A. Weinberg, Whitehead Institute);

v-Abl, V01541 (courtesy of George Q. Daley, Whitehead Institute); hIL-6, X04602 (cloned from RNA by Scott K. Dessain and Jennifer B. Stevens); p53, NM_000546 (the DD allele is courtesy of Moshe Oren, Weizmann Institute of Science, Rehovot, Israel).

Example 1

Expression of Ectopic Genes in Murine and Human Myeloma Cell Lines

Genes were ectopically expressed in human and murine myeloma cell lines utilizing standard techniques of retroviral gene transduction, as previously described. An ectopic hTERT gene or retroviral vector sequences were introduced into the SP2/0 mIL-6 murine myeloma cell line, creating the cell lines SP2/0 mIL-6 MP-hTERT and SP2/0 MP. RT-PCR was performed (as described above) to assess the presence of ectopic expression of human telomerase in the cell line SP2/0 mIL-6. FIG. 1 shows ectopic hTERT expression in the band in the upper panel and GAPDH expression is shown in the lower panel, assayed as a positive control for the presence of intact RNA.

An ectopic human IL-6 gene was introduced into the murine myeloma cell line, SP2/0 MP-hTERT, creating the polyclonal cell line SP2/0 MP-hTERT-hIL-6. Expression of the protein was verified by ELISA assay. These cells were also cloned, creating the clonal cell lines SP2/0 MP-hTERT-hIL-6 C9, F11, and F12.

Figure 2:
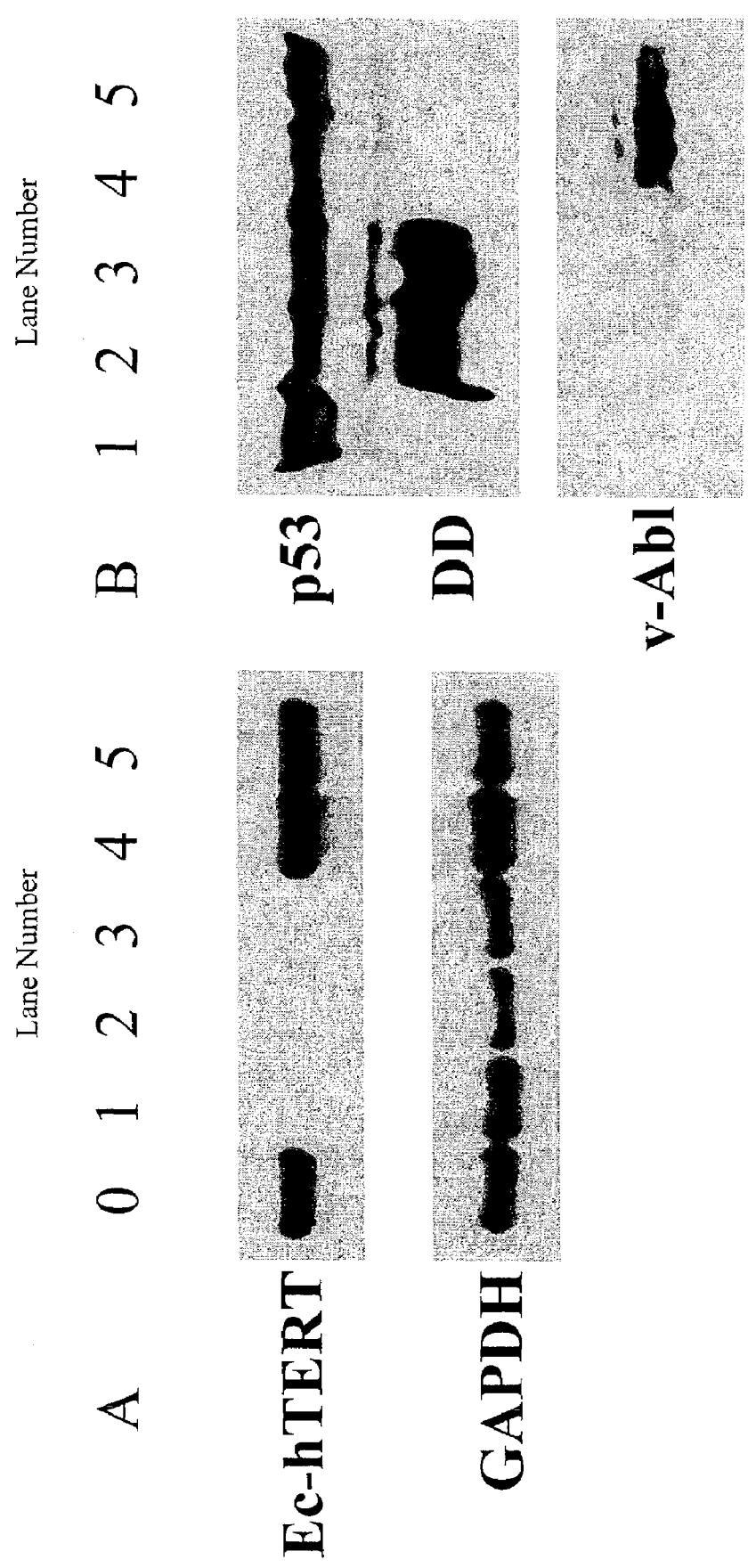
FIG. 2 shows an assessment of retrovirus-mediated ectopic gene expression in the J3 human myeloma cell line.

Retrovirus-mediated ectopic gene expression in the J3 human myeloma cell line was examined by introducing various genes into the SKO-007 J3 human myeloma cell line (J3). An ectopic DD gene, a gene that encodes only the tetramerization domain of p53 and acts as a dominant-negative inhibitor of p53 activity, was introduced into J3, creating the cell line, J3 DD. Either an ectopic human IL-6 gene or viral vector sequences were introduced into J3 DD, creating the cell lines J3 DD hIL-6 and J3 DD MIG. FIG. 2 illustrates RT-PCR performed as described above and in FIG. 1. The upper panel of FIG. 2 shows ectopic hTERT mRNA, the lower panel depicts GAPDH. The presence of p53 protein and the ectopically expressed DD mutant p53 protein was also determined by Western Blot using standard procedures. In additional experiments, an ectopic hTERT gene was introduced into the J3 DD hIL-6 and J3 DD MIG cell lines, creating J3 DD hIL-6 MP-hTERT and J3 DD MIG-hTERT.

The v-abl gene and the human telomerase gene were expressed in the J3 cell line, creating the cell line, J3 TA. The lower panel of FIG. 2 depicts a Western blot of the v-Abl protein. The human IL-6 gene or viral vector sequences were introduced into J3 TA, creating the cell lines, J3 TA hIL-6 and J3 TA MIG. Additional genes are also introduced into the J3 TA hIL-6 cell line. In one experiment, the hDM2 gene is introduced. In another experiment, an SV40 early region gene segment that encodes the SV40 large T and small T antigens is introduced. In additional experiments, retroviral transfer vectors encoding the genes: c-myc, interleukin-11, bcl-2, bclX-L, or Id-1 are introduced into the modified J3 cell lines.

The human IL-6 gene was cloned using reverse-transcriptase PCR from the human bladder carcinoma cell line, T24. The human IL-6 gene was subcloned into a retroviral transfer vector, pMSCV-IRES-GFP (MIG), which directs expression of the hIL-6 gene and a Green Fluorescent Protein gene from a bi-cistronic mRNA. The retroviral gene plasmid that encodes human IL-6 and GFP (green fluorescent protein gene) from a bi-cistronic mRNA is diagramed in FIG. 3, which schematically shows the relevant domains of the plasmid, pMSCV IRES GFP hIL-6. In the plasmid components include: MSCV LTR, with the LTR of the murine stem cell virus; hIL-6 is the human IL-6 gene; IRES is an internal ribosome entry site; and GFP is the green fluorescent protein gene.

Example 2

Figure 4:
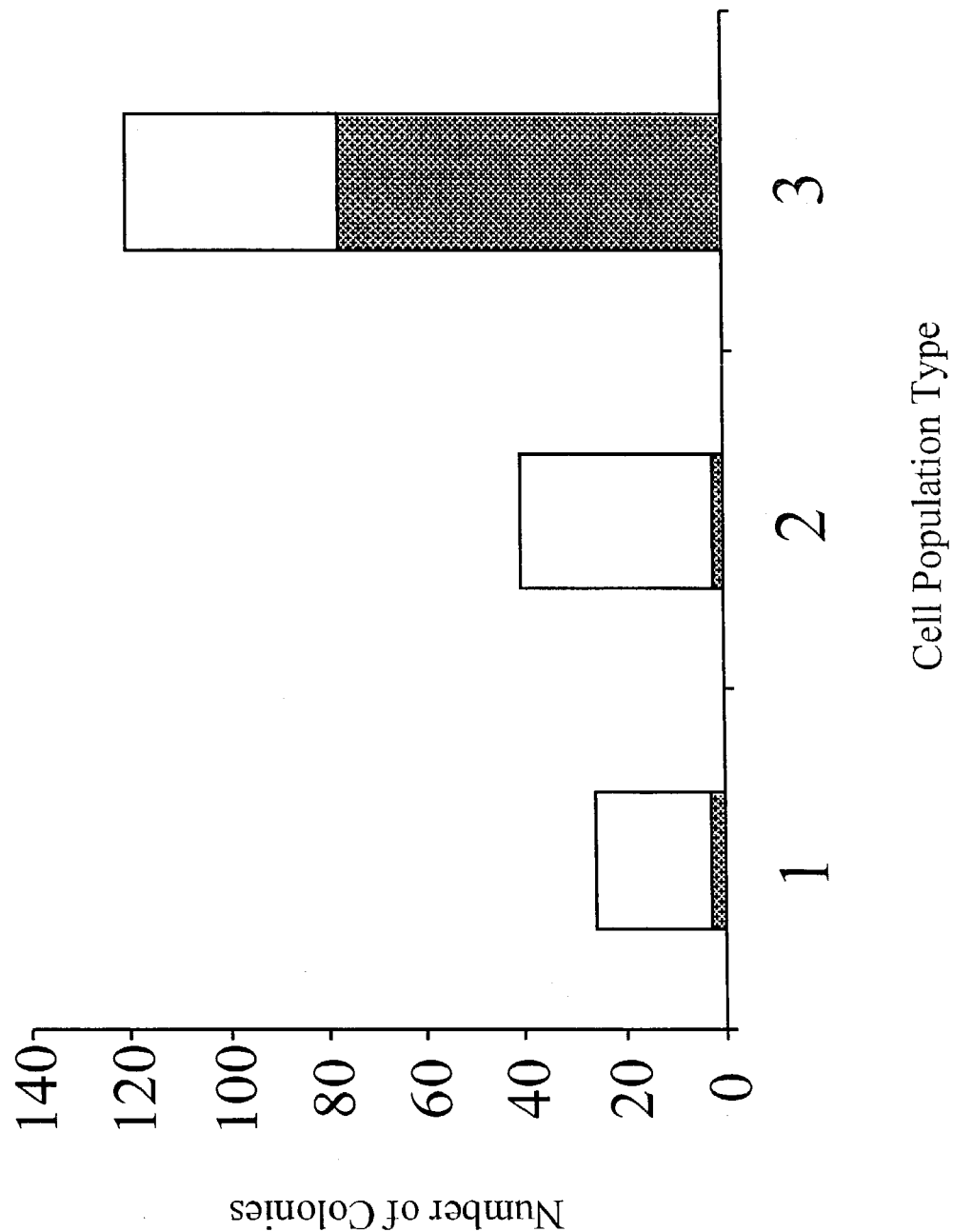
FIG. 4 shows a bar graph illustrating that IL-6 stimulates cloning and antibody production in murine/human hybrid cells. Cell fusions were performed between human splenocytes and the cell lines SP2/0 MP (Bar 1), SP2/0 MP-hTERT (Bar 2), and SP2/0 mIL-6 MP-hTERT (Bar 3). Hybrid cell populations that survived drug selection in HAT were cloned by limiting dilution. Colony counts are depicted; the numbers of colonies that were positive for human immunoglobulin secretion are denoted as shaded portions of the graph.

IL-6 Stimulates Cloning and Antibody Production in Murine/Human Hybrid Cells The ability to clone hybrid cells by limiting dilution is important for the creation of monoclonal cell lines and the monoclonal antibodies they produce. The fusion partner cell line SP2/0 mIL-6 MP-hTERT was fused to primary splenocytes and cultured in HAT-selection medium using standard techniques. The hybrid cell populations were cloned by limiting dilution into 96-well plates. Following cell fusion, wells containing hybrid cells formed with either the SP2/0, SP2/0 MP-hTERT, and SP2/0 mIL-6 MP-hTERT cells and human B-cells were plated at a density of 1, 5, and 10 cells per well. The number of clones arising following limiting dilution was counted. Each of the clones was tested for expression of human immunoglobulin protein. The total number of clones growing and the number of clones expressing immunoglobulin protein are depicted in FIG. 4. The SP2/0 mIL-6 MP-hTERT cell line is compared to the parental SP2/0 cell line containing retroviral vector control sequences only (Lane 1) or retroviral sequences encoding an ectopic hTERT gene (Lane 2). The fusion partner cell line SP2/0 mIL-6 MP-hTERT (Lane 3) allowed the creation of substantially more viable clones as well as a dramatic increase in the proportion of clones that make human immunoglobulin. This indicates that mIL-6 improves the viability of hybrid cells formed between murine myeloma cells and primary human B-lymphocytes and aids in the maintenance of the immunoglobulin-secretion phenotype. This procedure was repeated using SP2/0 cells that express hIL-6 and an ectopic human telomerase gene (the C9 clone, see above), fusing the cells to splenocytes. In the presence of murine thymocyte feeder layers, the ability of the C9 clone to form human antibody-secreting hybridomas was comparable to that seen with the SP2/0 mIL-6 MPT cell line. This indicates that non-murine IL-6 proteins that activate the murine IL-6R (such as the human IL-6 protein) can also improve the formation and phenotype of murine/human hybrid cells that make human monoclonal antibodies.

Figure 5:
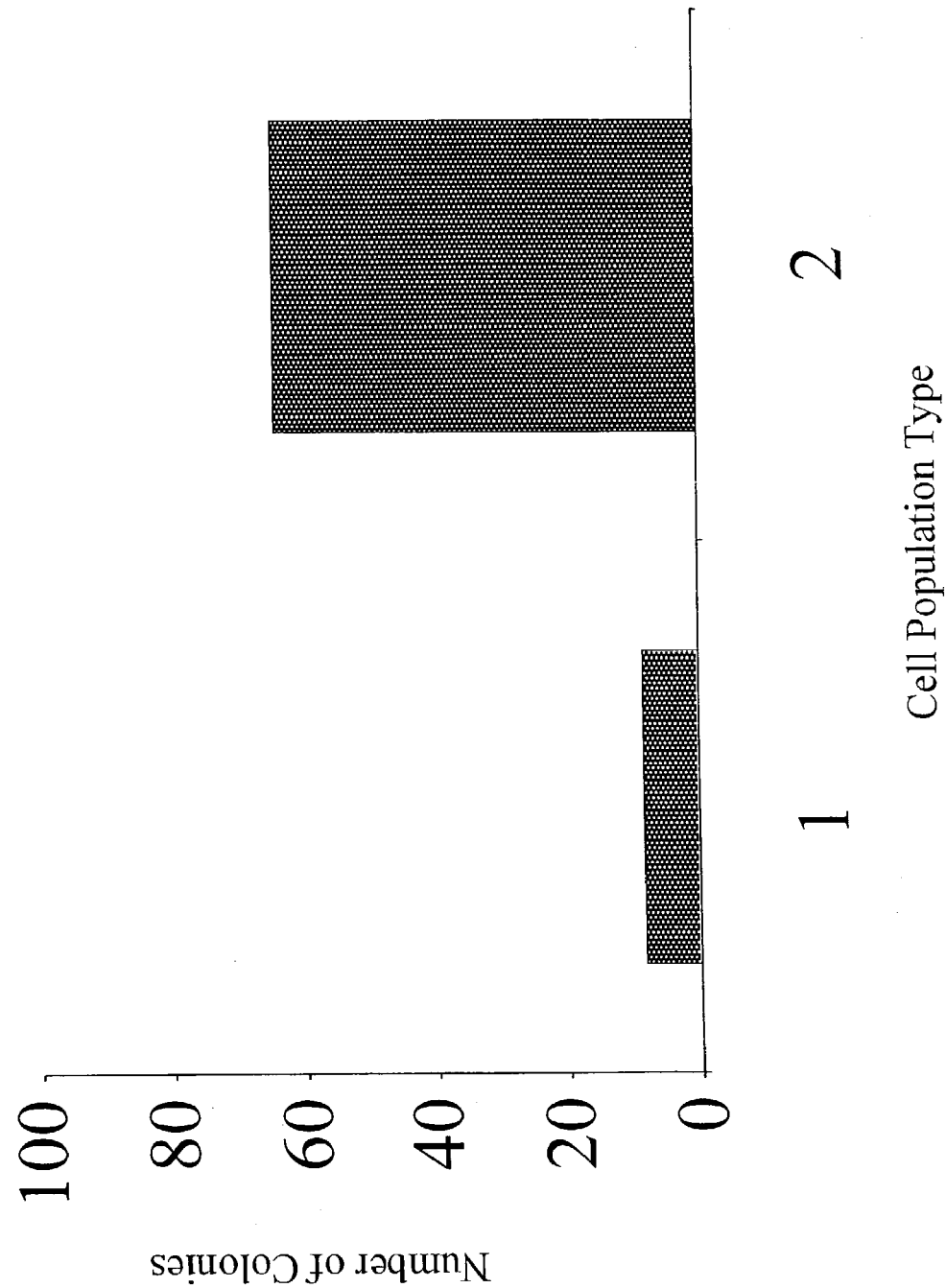
FIG. 5 is a bar graph illustrating that mIL-6 increases the percent of hybrid cell populations that yielded clones secreting high amounts of immunoglobulin. Cell populations were cloned by limiting dilution as described herein. The proportions of populations giving rise to clones that secreted high amounts of immunoglobulin are depicted in the bar graph: Bar 1, SP2/0 without mIL-6; Bar 2, SP2/0 with mIL-6.

Example 3 mIL-6 Increases the Percent of Hybrid Cell Populations that Yielded Clones Secreting High Amounts of Immunoglobulin In a repeat of the experiment described in Example 2, hybrid cell populations created between human splenocytes and SP2/0 fusion partner cell lines with and without ectopic mIL-6 expression were cloned by limiting dilution as described above. Growing clones were tested for immunoglobulin expression. Some of the clones expressed a high level of immunoglobulin, as indicated by a very deep color on ELISA assay that arose within seconds of adding the detection reagent. The proportion of hybrid cell populations that gave rise to clones expressing a high level of immunoglobulin is depicted in FIG. 5. The mIL-6-expressing populations gave rise to significantly more high-expressing clones than did populations formed without mIL-6. This indicates that mIL-6 increases the level of immunoglobulin secreted and the maintenance of that phenotype by hybrid cells formed between murine myeloma cells and primary human B-lymphocytes.

Example 4

Murine/Human Hybrid Cells Secrete Antibody Following Re-Cloning

Figure 6:
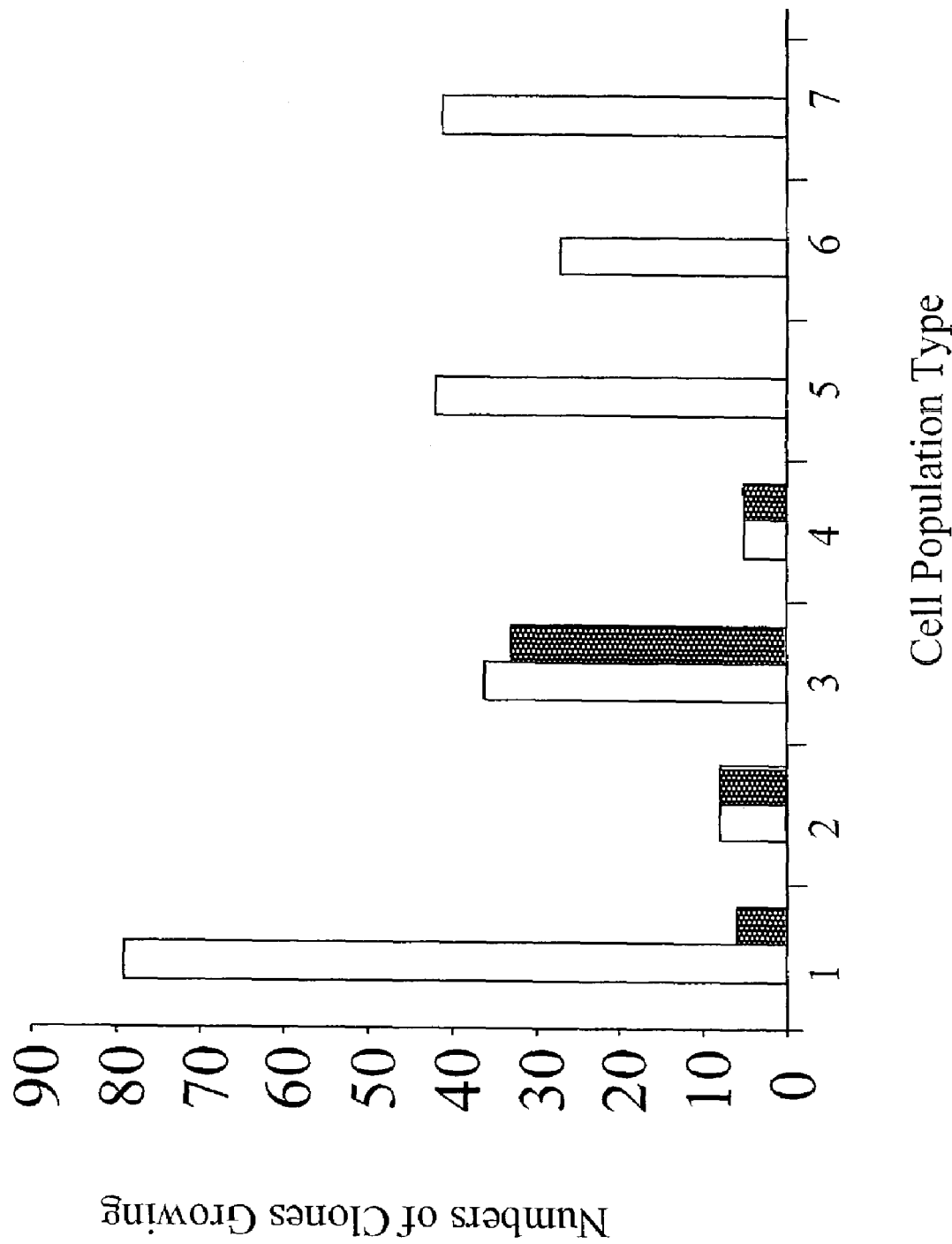
FIG. 6 is a bar graph illustrating that murine/human hybrid cells secrete antibody following re-cloning. High-immunoglobulin-secreting cell populations identified in Example 3 were cloned a second time by limiting dilution. The y-axis shows the numbers of clones growing, depicted with the white bars; the numbers of clones expressing antibody following re-cloning are depicted in shaded bars adjacent to the white bars. Each numbered pair of bars represents a single re-cloned cell line. Clones 5, 6, and 7 gave no antibody-positive clones.

Some of the high immunoglobulin-expressing clones described in Example 3 were cloned a second time by limiting dilution as described above. All of the seven clones could be re-cloned, and four of seven of the clones expressed antibody following re-cloning, indicating the novel and considerable stability of the immunoglobulin secretion phenotype expressed by hybrid cells expressing mIL-6 (FIG. 6).

Example 5

Ectopic hTERT Improves Cloning of Murine/Human mIL-6 Hybrid Cell Populations

Figure 7:
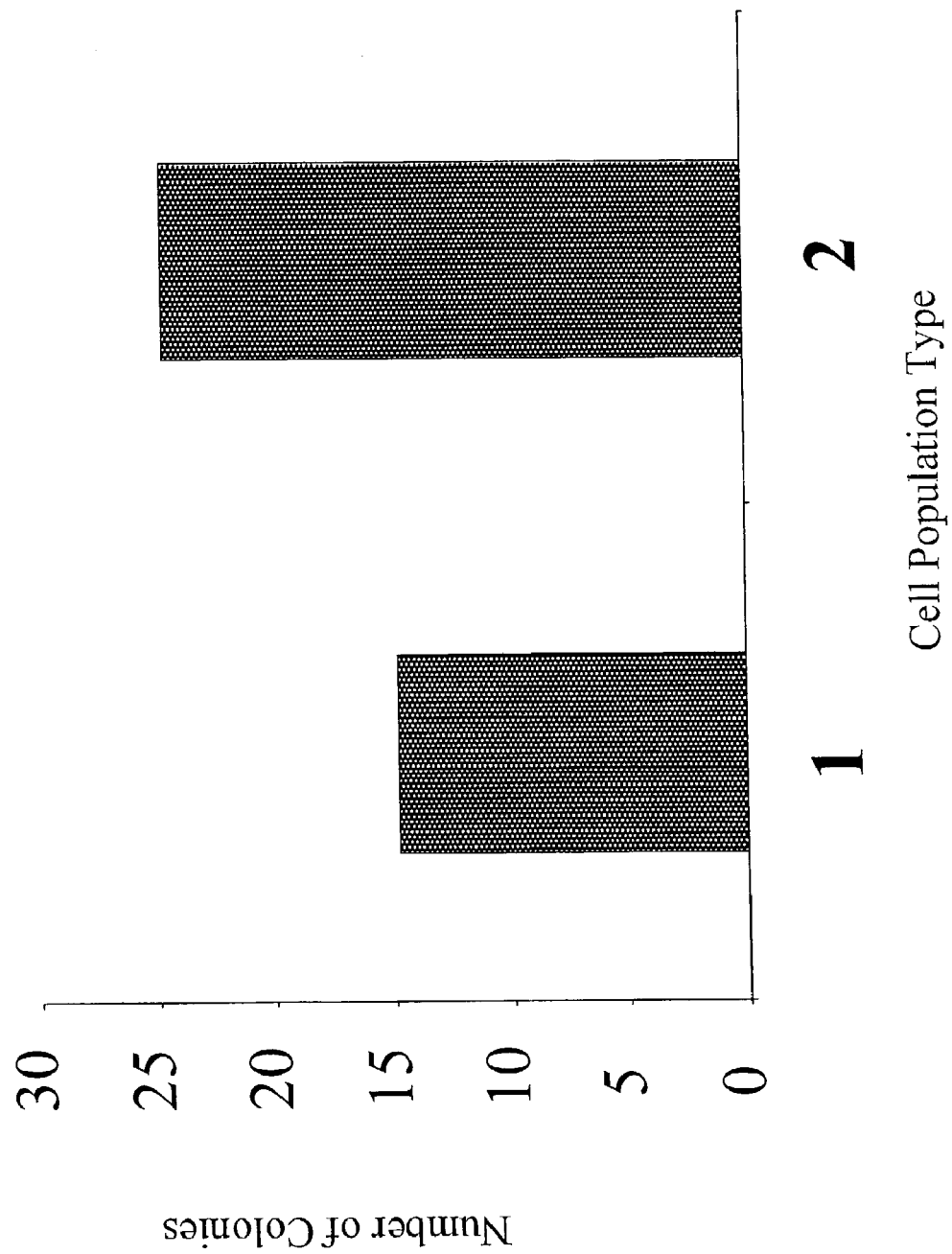
FIG. 7 is a bar graph illustrating that ectopic hTERT improves cloning of murine/human mIL-6 hybrid cell populations. Hybrid cell populations expressing mIL-6 with (Bar 2) and without (Bar 1) ectopic human telomerase were formed by fusion with human splenocytes. After approximately 2 weeks following HAT selection, the cells in each well were counted; the mean numbers of cells in each well is shown in the bar graph. The counts are given as cells×$10^3$/milliliter.

In the experiment described in Example 3, cell populations were generated with SP2/0 mIL-6 fusion partner cells with and without ectopic human telomerase expression. Cell populations were cloned by limiting dilution (as described above), and the average numbers of clones arising from populations with and without hTERT were determined. Hybrid cell populations expressing mIL-6 with and without ectopic human telomerase were formed by fusion with human splenocytes. Approximately 2 weeks following HAT selection, the cells in each well were counted, the mean numbers in each well is shown in FIG. 7. The ability of mIL-6 expression to improve the viability of murine/human hybrid cell clones is distinct from and contributory to the improvement provided by ectopic hTERT expression.

Example 6

Figure 8:
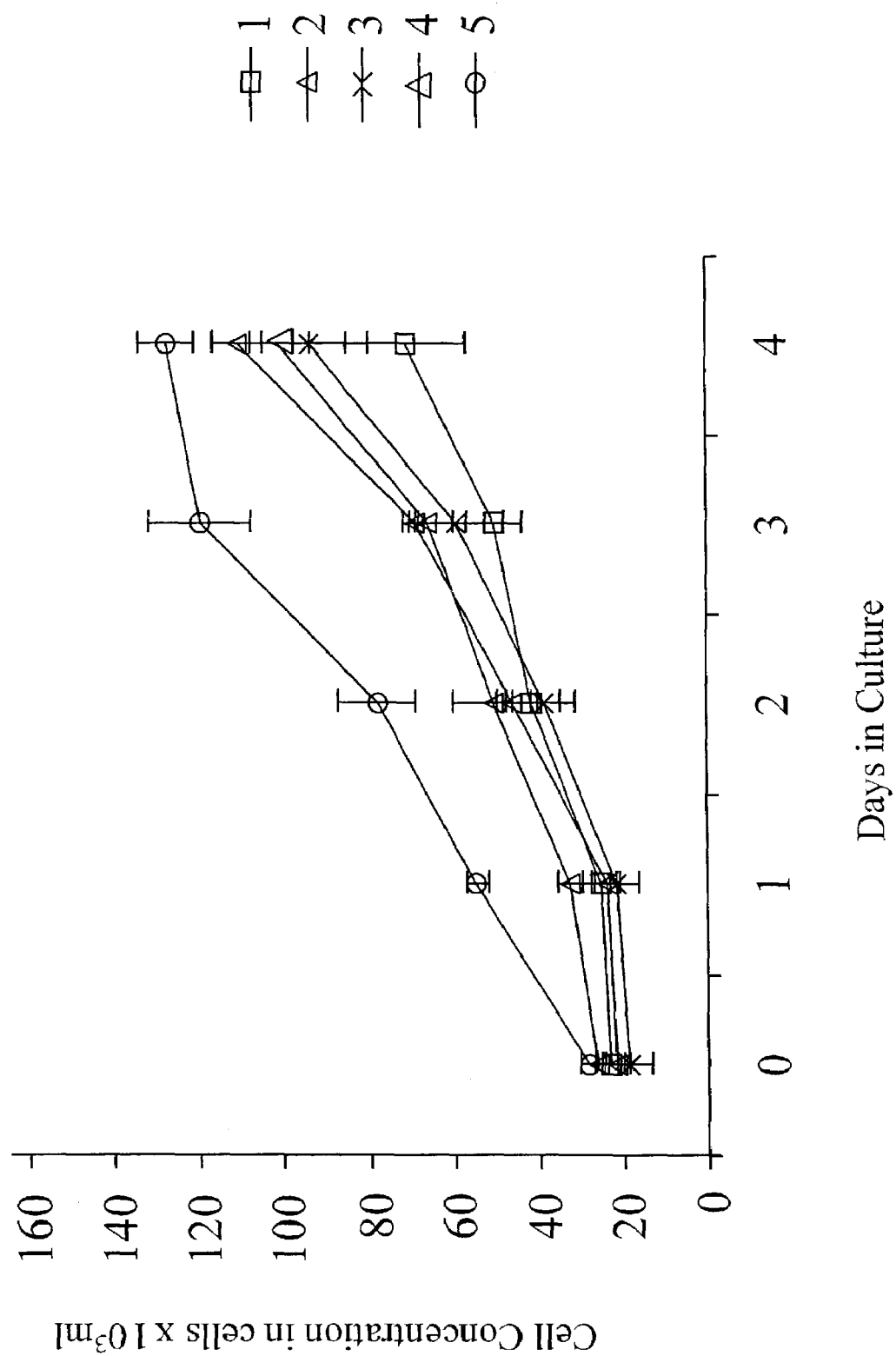
FIG. 8 is a line graph of growth curves of cell lines derived from the SKO-007 J3 cell line. The J3 cell lines described in Example 1 were plated in triplicate and counted daily. The y-axis denotes the concentration of cells, given as cells×$10^3$/milliliter. The x-axis denotes the days in culture. Square, J3; small triangle, J3 DD MIG; cross, J3 DD hIL-6; large triangle, J3 TA MIG; circle, J3 TA hIL-6.

Human IL-6 and v-Abl Expression Improves the Growth Rate of the J3 Myeloma Cell Lines Expressing Human Telomerase The retrovirally transduced J3 cell lines described in Example 1 were plated in triplicate, counted daily, and their growth rates compared (FIG. 8). The cell line expressing human telomerase, v-Abl, and human IL-6 (J3 TA hIL-6) had a population doubling time almost twice that of the parental J3 cell line. Because the J3 TA hIL-6 line grew better than the J3 TA cell line, it is evident that the combination of v-Abl and hIL-6 is necessary for the observed rapid growth phenotype. The cell lines J3 DD, J3 DD hIL-6, and J3 TA all exhibited an improved growth rate relative to the parental J3 cell line. Such improvements in the growth rate will dramatically improve the utility of fusion partner cell lines in producing human immunoglobulin secreting hybridomas.

Example 7

Figure 9:
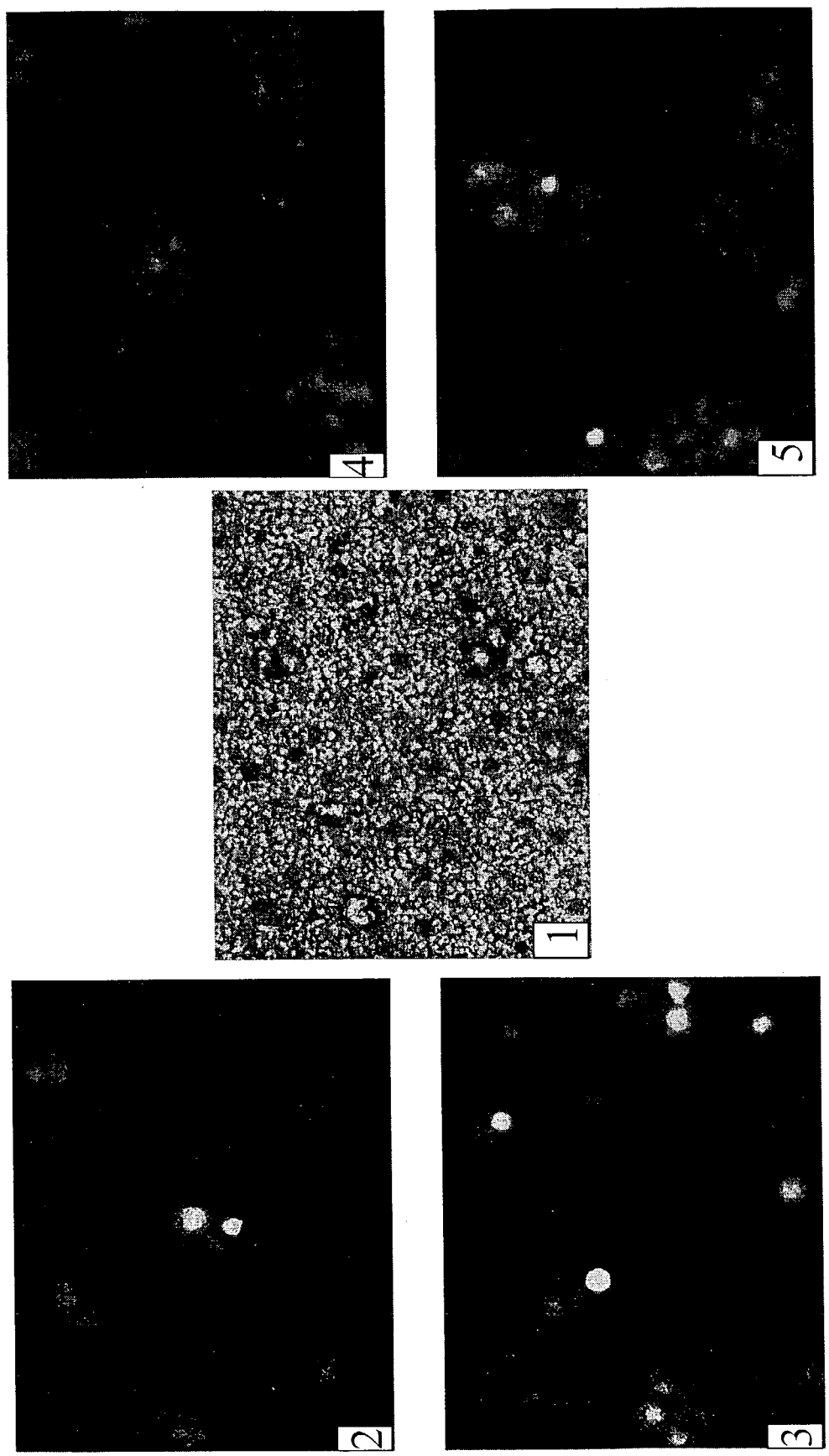
FIG. 9 shows digitized photomicrographic images demonstrating that ectopic hTERT and IL-6 expression improve the establishment of J3/splenocyte hybrid cells. Photomicrographs are shown of early hybrid cell populations formed between the retrovirally-transduced J3 cell lines described in Example 1 and primary human splenocytes. The cells are shown following HAT selection and approximately 4 weeks following cell fusion. The J3 control cell population is depicted in bright-field because the J3 cell line does not express a GFP gene; the others are shown by fluorescence microscopy. Panel 1, J3; panel 2, J3 DD MIG; panel 3, J3 DD hIL-6; panel 4, J3 TA MIG; panel 5, J3 TA hIL-6.
Figure 10:
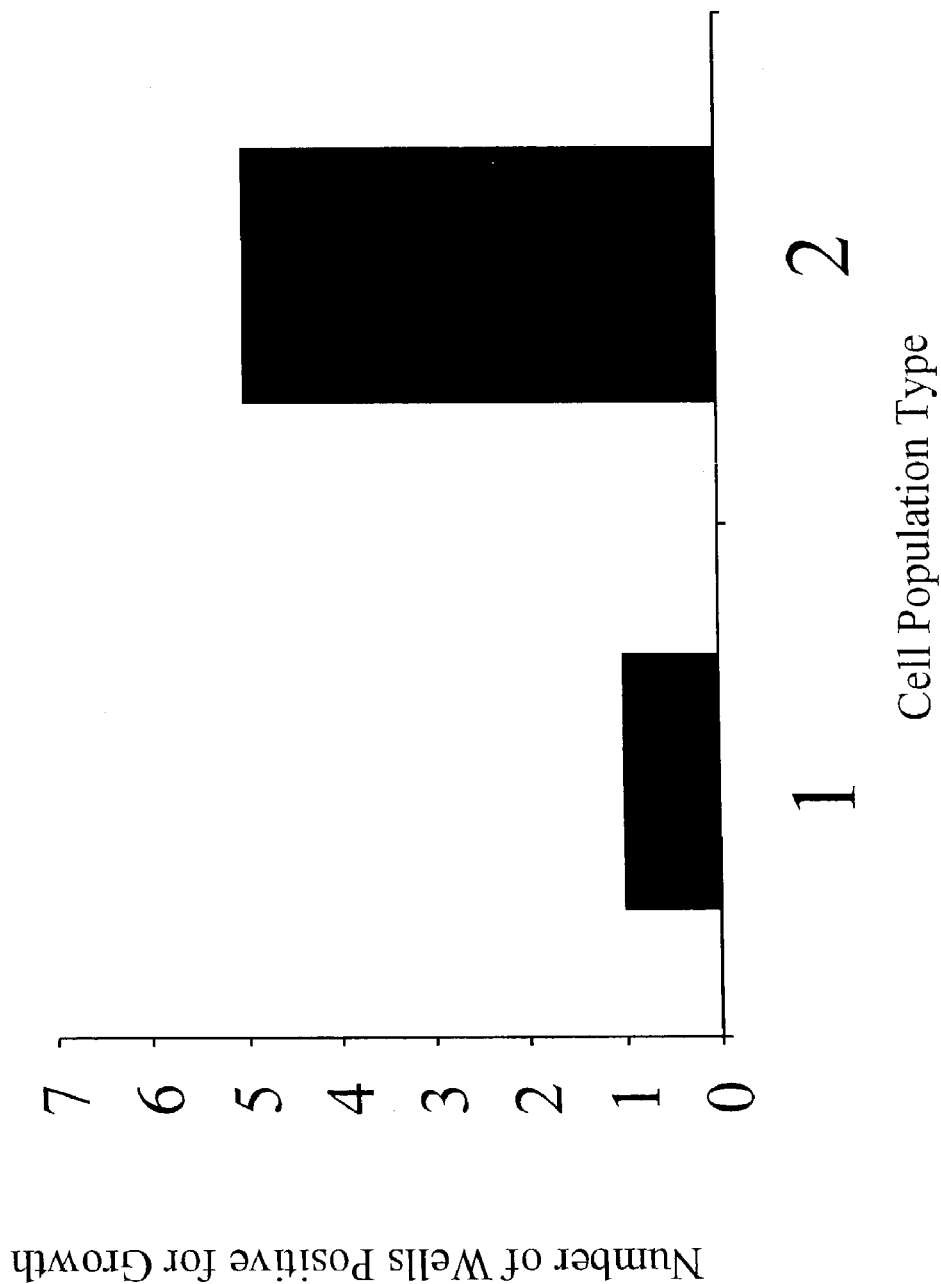
FIG. 10 is a bar graph illustrating that ectopic expression of a protein that inhibits p53 function in an immortal human fusion partner cell line improves the establishment of hybrid cell populations. The J3 cell line expressing the DD dominant-negative p53 allele and the GFP protein were fused to primary human splenocytes, selected, and observed for growth. After approximately 6 weeks, color change of the growth medium and visible cell growth were observed in 5 of 7 wells containing the DD-expressing cell line (Bar 2). Only one out of 7 control wells, containing J3 cells without DD or GFP expression, had evidence of growth (Bar 1). The y axis indicates the number of wells positive for growth (out of 7 plated).

Ectopic hTERT and IL-6 Expression Improve the Establishment of J3/Splenocyte Hybrid Cells A cell fusion experiment was performed using the retrovirally modified J3 human myeloma cell lines described in Example 1 with primary human splenocytes. Following HAT selection, small colonies became visible at approximately 4 weeks. Comparing the appearance of the cultures suggested that the growth of hybrid cells formed with the hTERT-expressing lines are superior to the other lines (FIG. 9). Similarly, the J3 DD hIL-6 cell line appeared to form hybrids more effectively than the J3 DD cell line. Small numbers of cells were visible in the J3 fusion population, comparable to what was seen with the J3 DD population. The J3 cell line is depicted here in a bright-field photomicrograph because it does not express a retroviral GFP gene.

In a repeat experiment, abundant hybrid cells formed between J3 TA hIL-6 cell line and human splenocytes were visible following 10 days of HAT selection, whereas virtually no growth was seen in the J3 parental cell line/human splenocyte fusion or in control, unfused J3 TA hIL-6 cells treated with HAT selection medium. This indicates that ectopic hTERT and IL-6 expression improve the establishment of J3/splenocyte hybrid cells. As was noted previously, these hybrid cells grew slowly, suggesting that the ectopic expression of additional dominant genes in the fusion partner cell lines may confer further benefits to the hybrid cells.

Example 8

Ectopic Expression of a Protein that Inhibits p53 Function in an Immortal Human Fusion Partner Cell Line Improves the Establishment of Hybrid Cell Populations Observation at 6 weeks of the J3 and J3 DD hybrid cells described in Example 7 revealed significant growth in 5/7 of the hybrid wells containing the J3 DD fusion partner cell line, but significant growth in only 1/7 of the wells containing the control J3 cell line. All of the cell populations secreted human immunoglobulin by ELISA. Wells containing the other three GFP positive cell lines (J3 DD hIL-6, J3 TA, J3 TA hIL-6) had apparently viable cells but much less proliferation. J3 TA cells also expressed human antibody by ELISA. Early observation of cloning of the J3 DD/splenocyte hybrid cells by limiting dilution indicates robust growth of many clones.

Example 9

The SP2/0 mIL-6 MPT Cell Line Effectively Forms Human Immunoglobulin-Secreting Hybrid Cells when Fused to Human Peripheral Blood Lymphocytes The SP2/0 mIL-6 MPT cell line was fused following standard techniques to peripheral blood lymphocytes that had been stimulated with pokeweed mitogen for 5 days. Flow cytometry indicated that the population consisted of approximately 7% stimulated human B-lymphocytes. At a plating density of $10^5$ cells/well, 31% of the wells were positive for hybrid cells secreting human immunoglobulin. This gives a rate of hybridoma formation of slightly less than 1 immunoglobulin-secreting hybridoma per 7000 human B-lymphocytes.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

All patents, patent applications and references disclosed herein are incorporated by reference in their entirety.

What is claimed is:

1. A mouse B-lineage fusion partner cell comprising at least two ectopically expressed exogenous nucleic acid molecules, wherein
   (a) each of the ectopically expressed nucleic acid molecules encodes a polypeptide that when expressed in a hybrid cell formed by the fusion of the fusion partner cell and a human B-lineage fusion cell, alters the phenotype of the hybrid cell;
   (b) one of the at least two encoded polypeptides is IL-6 or IL-11, and one of the encoded polypeptides is hTERT; and
   (c) the fusion partner cell is characterized in that fusion of the fusion partner cell with the human B-lineage fusion cell results in a hybrid cell that displays enhanced stability of antibody expression upon cloning of the hybrid cell, relative to the stability of antibody expression that would be observed if the fusion partner cell ectopically expressed IL-6 or hTERT but not both.

2. The mouse B-lineage fusion partner cell of claim 1, wherein the B-lineage fusion partner cell is a myeloma or lymphoblastoid fusion partner cell.

3. A human B-lineage fusion partner cell comprising at least two ectopically expressed exogenous nucleic acid molecules, wherein
   (a) each of the ectopically expressed nucleic acid molecules encodes a polypeptide that when expressed in a hybrid cell formed by the fusion of the fusion partner cell and a fusion cell, alters the phenotype of the hybrid cell, and
   (b) one of the at least two encoded polypeptides is IL-6 or IL-11, and one of the encoded polypeptides is hTERT.

4. The human B-lineage fusion partner cell of claim 3, wherein the fusion cell is a human B-lineage cell.

5. The human B-lineage fusion partner cell of claim 3, wherein the fusion partner cell is a myeloma cell.

6. The human B-lineage fusion partner cell of claim 3, wherein the at least two ectopically expressed nucleic acid molecules are expressed from one or more exogenously introduced expression cassettes.

7. The human B-lineage fusion partner cell of claim 6, wherein the cassettes are included in viral vectors.

8. The human B-lineage fusion partner cell of claim 6, wherein the cassettes are included in plasmid vectors.

9. The human B-lineage fusion partner cell of claim 7, wherein the vectors are not integrated in one or more chromosomes.

10. The human B-lineage fusion partner cell of claim 6, wherein the cassettes are integrated in one or more chromosomes.

11. The human B-lineage fusion partner cell of claim 6, wherein there is more than one cassette, and wherein each cassette comprises at least one constitutive promoter operably linked to a nucleic acid molecule.

12. The human B-lineage fusion partner cell of claim 3, wherein the B-lineage fusion partner cell is a myeloma or lymphoblastoid fusion partner cell.

13. A mammalian B-lineage fusion partner cell comprising at least two ectopically expressed exogenous nucleic acid molecules, wherein
   (a) each of the ectopically expressed nucleic acid molecules encodes a polypeptide that when expressed in a hybrid cell formed by the fusion of the fusion partner cell and a fusion cell, alters the phenotype of the hybrid cell;
   (b) one of the at least two encoded polypeptides is IL-6 or IL-11, and one of the encoded polypeptides is hTERT;
   (c) the at least two ectopically expressed nucleic acid molecules are expressed from one or more exogenously introduced expression cassettes; and
   (d) there is more than one cassette, and each cassette comprises at least one regulatable promoter operably linked to a nucleic acid molecule.

14. The mammalian B-lineage fusion partner cell of claim 13, wherein the B-lineage fusion partner cell is a myeloma or lymphoblastoid fusion partner cell.

15. A mouse B-linage fusion partner cell comprising a soluble or membrane bound growth factor selected from the group consisting of IL-6 and IL-11 and at least one ectopically expressed exogenous nucleic acid molecule that encodes at least one polypeptide that when expressed in a hybrid cell formed by the fusion of the fusion partner cell and a human B-lineage fusion cell, alters the phenotype of the hybrid cell, wherein
   (a) at least one encoded polypeptide is hTERT; and
   (b) the fusion partner cell is characterized in that fusion of the fusion partner cell with the human B-lineage fusion cell results in a hybrid cell that displays enhanced stability of antibody expression upon cloning of the hybrid cell, relative to the stability of antibody expression that would be observed if the fusion partner cell did not ectopically express hTERT.

16. The mouse B-lineage fusion partner cell of claim 15, wherein the B-lineage fusion partner cell is a myeloma or lymphoblastoid fusion partner cell.

17. A mammalian B-lineage fusion partner cell comprising a soluble or membrane bound growth factor selected from the group consisting of IL-6 and IL-11 and at least one ectopically expressed exogenous nucleic acid molecule that encodes at least one polypeptide that when expressed in a hybrid cell formed by the fusion of the fusion partner cell and a human B-lineage fusion cell, alters the phenotype of the hybrid cell, wherein
   (a) at least one encoded polypeptide is hTERT; and
   (b) the fusion partner cell is characterized in that fusion of the fusion partner cell with the human B-lineage fusion cell results in a hybrid cell that displays enhanced stability of antibody expression upon cloning of the hybrid cell, relative to the stability of antibody expression that would be observed if the fusion partner cell did not ectopically express hTERT.

18. The mammalian B-lineage fusion partner cell of claim 17, wherein the B-lineage fusion partner cell is a myeloma or lymphoblastoid fusion partner cell.

19. A mouse B-lineage fusion partner cell comprising a soluble or membrane bound growth factor selected from the group consisting of IL-6 and IL-11 and at least one ectopically expressed exogenous nucleic acid molecule that encodes at least one polypeptide that when expressed in a hybrid cell formed by the fusion of the fusion partner cell and a primary human B-lineage fusion cell, alters the phenotype of the hybrid cell, wherein;
  (a) at least one encoded polypeptide is hTERT; and
  (b) the fusion partner cell is characterized in that fusion of the fusion partner cell with the primary human B-lineage fusion cell results in a hybrid cell that displays enhanced stability of antibody expression upon cloning of the hybrid cell, relative to the stability of antibody expression that would be observed if the fusion partner cell did not ectopically express hTERT.

20. The mouse B-lineage fusion partner cell of claim 19, wherein the B-lineage fusion partner cell is a myeloma or lymphoblastoid fusion partner cell.

21. A mouse B-lineage fusion partner cell comprising at least two ectopically expressed exogenous nucleic acid molecules, wherein
  (a) each of the ectopically expressed nucleic acid molecules encodes a polypeptide that when expressed in a hybrid cell formed by the fusion of the fusion partner cell and a primary human B-lineage fusion cell, alters the phenotype of the hybrid cell;
  (b) one of the at least two encoded polypeptides is IL-6 or IL-11, and one of the encoded polypeptides is hTERT; and
  (c) the fusion partner cell is characterized in that fusion of the fusion partner cell with the primary human B-lineage fusion cell results in a hybrid cell that displays enhanced stability of antibody expression upon cloning of the hybrid cell, relative to the stability of antibody expression that would be observed if the fusion partner cell ectopically expressed IL-6 or hTERT but not both.

22. The mouse B-lineage fusion partner cell of claim 21, wherein the B-lineage fusion partner cell is a myeloma or lymphoblastoid fusion partner cell.

23. A mammalian B-lineage fusion partner cell comprising at least two ectopically expressed exogenous nucleic acid molecules, wherein
  (a) each of the ectopically expressed nucleic acid molecules encodes a polypeptide that when expressed in a hybrid cell formed by the fusion of the fusion partner cell and a human B-lineage fusion cell, alters the phenotype of the hybrid cell;
  (b) one of the at least two encoded polypeptides is IL-6 or IL-11, and one of the encoded polypeptides is hTERT; and
  (c) the fusion partner cell is characterized in that fusion of the fusion partner cell with the human B-lineage fusion cell results in a hybrid cell that displays enhanced stability of antibody expression upon cloning of the hybrid cell; relative to the stability of antibody expression that would be observed if the fusion partner cell ectopically expressed IL-6 or hTERT but not both.

24. The mammalian B-lineage fusion partner cell of claim 23, wherein the B-lineage fusion partner cell is a myeloma or lymphoblastoid fusion partner cell.

\* \* \* \* \*